US012779107B2

(12) United States Patent
Klitmose et al.

(10) Patent No.: US 12,779,107 B2
(45) Date of Patent: Nov. 3, 2026

(54) SYRINGE HOLDER FOR A MEDICAL INJECTOR AND METHOD OF FORMING A MEDICAL INJECTOR ASSEMBLY

(71) Applicant: Novo Nordisk A/S, Bagsvaerd (DK)

(72) Inventors: Lars Peter Klitmose, Gentofte (DK); Ebbe Kiilerich, Copenhagen NV (DK)

(73) Assignee: Novo Nordisk A/S, Bagsvaerd (DK)

(*) Notice: Subject to any disclaimer, the term of this patent is extended or adjusted under 35 U.S.C. 154(b) by 989 days.

(21) Appl. No.: 16/759,480

(22) PCT Filed: Oct. 24, 2018

(86) PCT No.: PCT/EP2018/079151
§ 371 (c)(1),
(2) Date: Apr. 27, 2020

(87) PCT Pub. No.: WO2019/081578
PCT Pub. Date: May 2, 2019

(65) Prior Publication Data

US 2020/0330676 A1 Oct. 22, 2020

(30) Foreign Application Priority Data

Oct. 28, 2017 (EP) .................................... 17199066
Feb. 18, 2018 (EP) .................................... 18157292

(51) Int. Cl.
*A61M 5/00* (2006.01)
*A61M 5/31* (2006.01)
*A61M 5/32* (2006.01)

(52) U.S. Cl.
CPC .......... *A61M 5/002* (2013.01); *A61M 5/3129* (2013.01); *A61M 5/3202* (2013.01); *A61M 2207/00* (2013.01)

(58) Field of Classification Search
CPC .. A61M 5/002; A61M 5/3129; A61M 5/3202; A61M 2207/00;
(Continued)

(56) References Cited

U.S. PATENT DOCUMENTS 5,226,894 A * 7/1993 Haber ................ A61M 5/3243 604/240
6,726,657 B1 * 4/2004 Dedig ................ A61M 5/1456 604/152
(Continued)

FOREIGN PATENT DOCUMENTS

CN 107106769 A 8/2017
DE 202016100531 U1 2/2016
(Continued)

*Primary Examiner* — Chelsea E Stinson
*Assistant Examiner* — Erica A Lange
(74) *Attorney, Agent, or Firm* — Elizabeth A. Dingess-Hammond

(57) ABSTRACT

A syringe holder (200) comprising: a body (210) extending along a central longitudinal axis and adapted to receive the barrel (110) of a syringe (100), wherein the body (210) includes at least two body sections (240) disposed around the central longitudinal axis, the body sections (240, 240A, 240B) having distal ends with shoulder sections (250) adapted for being received in a circumferential gap (150) between the barrel (110) of the syringe (100) and a needle shield (120) covering a needle (130) of the syringe to retain the syringe (100) so as to prevent the syringe from moving distally (D) relative to the syringe holder (200), wherein the body (210) further comprises a plurality of expandable connector arrangements (230) each interconnecting pairs of the at least two body sections (240, 240A, 240B) so that the body sections (240, 240A, 240B) and the expandable connector arrangements (230) form a closed loop in the circumferential direction around the barrel (110) of a syringe (100) held by the body (210), wherein the expandable
(Continued)

connector arrangements (230) are so configured that the body sections (240, 240A, 240B) are movable between a non-retaining position and a retaining position.

15 Claims, 12 Drawing Sheets

(58) Field of Classification Search
CPC ............ A61M 2005/2477; A61M 5/24; A61M 5/1456; A61M 2005/2407; A61M 2005/2433; A61M 2005/2485
See application file for complete search history.

(56) References Cited

U.S. PATENT DOCUMENTS

| | | | | |
|---|---|---|---|---|
| 8,647,299 | B2 | 2/2014 | Stamp | |
| 8,708,968 | B2 * | 4/2014 | Julian | A61M 5/321 604/192 |
| D766,426 | S * | 9/2016 | Hamann | D24/114 |
| 9,713,678 | B2 * | 7/2017 | Hourmand | A61M 5/24 |
| 10,213,559 | B2 | 2/2019 | Soerensen et al. | |
| 10,561,800 | B2 | 2/2020 | Marlin et al. | |
| 2001/0005781 | A1 | 6/2001 | Bergens et al. | |
| 2001/0011163 | A1 * | 8/2001 | Nolan, Jr. | A61M 5/1456 604/154 |
| 2009/0012471 | A1 | 1/2009 | Harrison | |
| 2010/0185178 | A1 | 7/2010 | Sharp et al. | |
| 2012/0203186 | A1 | 8/2012 | Vogt et al. | |
| 2014/0350479 | A1 * | 11/2014 | Hourmand | A61M 5/321 604/197 |
| 2016/0008542 | A1 * | 1/2016 | Hirschel | A61M 5/2033 604/137 |
| 2019/0015591 | A1 * | 1/2019 | Morlok | A61M 5/20 |
| 2019/0224416 | A1 | 7/2019 | Verpillere | |
| 2019/0290849 | A1 | 9/2019 | Hirschel et al. | |

FOREIGN PATENT DOCUMENTS

| | | | |
|---|---|---|---|
| EP | 2401009 | A1 | 1/2012 |
| EP | 2601988 | A1 | 6/2013 |
| EP | 2714144 | A2 | 4/2014 |
| EP | 2714157 | A2 | 4/2014 |
| EP | 2742962 | A2 | 6/2014 |
| EP | 2788052 | A1 | 10/2014 |
| EP | 2788055 | A1 | 10/2014 |
| EP | 3138595 | A1 | 3/2017 |
| EP | 3153197 | A1 | 4/2017 |
| JP | 3875346 | | 1/2007 |
| JP | 2016533219 | A | 10/2016 |
| WO | 0108727 | A1 | 2/2001 |
| WO | 2005115507 | | 12/2005 |
| WO | 2007083115 | | 7/2007 |
| WO | 2009127861 | | 10/2009 |
| WO | 2010084306 | | 7/2010 |
| WO | 2010/097116 | | 9/2010 |
| WO | 2010147553 | | 12/2010 |
| WO | 2011001161 | | 1/2011 |
| WO | 2011012849 | | 2/2011 |
| WO | 2012085585 | | 6/2012 |
| WO | 2010/164389 | | 12/2012 |
| WO | 2012/164404 | | 12/2012 |
| WO | 2013/083613 | | 6/2013 |
| WO | 2013083614 | | 6/2013 |
| WO | 2013089620 | | 6/2013 |
| WO | 2013156346 | | 10/2013 |
| WO | 2015022295 | | 2/2015 |
| WO | 2016193356 | | 12/2016 |
| WO | 2016193374 | | 12/2016 |
| WO | 2017071909 | | 5/2017 |
| WO | 2017140962 | | 8/2017 |
| WO | 2017153117 | | 9/2017 |
| WO | 2018015119 | | 1/2018 |

* cited by examiner

SYRINGE HOLDER FOR A MEDICAL INJECTOR AND METHOD OF FORMING A MEDICAL INJECTOR ASSEMBLY

CROSS-REFERENCE TO RELATED APPLICATIONS

This application is a 35 U.S.C. § 371 National Stage application of International Application PCT/EP2018/079151 (published as WO 2019/081578), filed Oct. 24, 2018, which claims priority to European Patent Applications EP 17199066.6, filed Oct. 28, 2017 and EP 18157292.6, filed Feb. 18, 2018; the contents of which are incorporated herein by reference.

The present invention relates to a syringe holder for a medical injector for injecting one or more doses of a liquid drug. In particular the present invention relates to syringe holders and methods for providing easy assembling of a syringe in a syringe holder.

BACKGROUND

In conventional handheld medical injectors standard prefilled syringes are often used for primary packaging. In order to provide particular functions for the medical injector, or to provide ease of handling and protection for the syringe, prefilled syringes are often accommodated in a syringe holder and inserted into an outer housing. Disposable medical injectors provide a particular user-friendly and inexpensive class of medical injectors, wherein a prefilled syringe is permanently held within the housing of the medical injector in a manner so that the syringe cannot be removed from the housing and thus do not enable reuse of the empty medical injector.

A conventional syringe holder provides shoulders that are adapted to engage a neck on the syringe and prevent the syringe from disengaging the syringe holder. Because syringes are generally supplied with rigid needle shields covering the needle and those needle shields have a diameter greater than a diameter between the shoulders, a separate assembly step is required—inserting the syringe in the syringe holder and then attaching the rigid needle shield to the needle.

The reference WO 2010/084306 suggests to insert and hold a syringe into a syringe holder being formed by first and second sections that are formed as discrete pieces that clip together after the syringe has been inserted. This reference also discloses a syringe holder having first and second sections that are connected to one another via a hinge, preferably a living hinge, along one set of the opposed longitudinal edges, which enables the syringe to be received between the open sections whereafter the sections are closed around the syringe.

In addition, references WO 2005/115507, WO 2007/083115 and WO 2013/083614 include disclosure of a variety of designs for syringe holders and syringe carriers. Many of the designs rely on the principle of having the needle shield contacting the syringe holder to expand resilient shoulder sections of the syringe holder in order to enable movement of the needle shield past the shoulder sections. This allows the syringe to be properly positioned in the syringe holder so that the shoulder sections become received in a circumferential gap between the needle shield and the barrel of the syringe. Due to the contact between the needle shield and the syringe holder the needle shield may become moved relative to the barrel of the syringe. This may introduce issues with respect to maintaining the needle area of the syringe in a sterile condition. Furthermore, many of the shown designs are not suitable for use in assembly operations in large scale manufacturing. Further examples of syringe holders are disclosed in WO01/08727 and DE 202016100531 U1 which both disclose injection devices wherein a syringe is held using a finger flange of the syringe to retain the syringe axially within the injection device.

SUMMARY

It is an object of the present invention to provide an improved syringe holder which protects a syringe held by the syringe holder and which enables improved manufacturability.

In the disclosure of the present invention, embodiments and aspects will be described which will address one or more of the above objects or which will address objects apparent from the below disclosure as well as from the description of exemplary embodiments.

In a first aspect, the present invention relates to a syringe holder comprising:

- a body extending along a central longitudinal axis and adapted to receive the barrel of a syringe, wherein the body includes at least two body sections disposed around the central longitudinal axis, the body sections having distal ends with shoulder sections adapted for being received in a circumferential gap between the barrel of the syringe and a needle shield covering a needle of the syringe to retain the syringe so as to prevent the syringe from moving distally (D) relative to the syringe holder, wherein the body further comprises a plurality of expandable connector arrangements which interconnect neighbouring pairs of the at least two body sections so that the body sections and the expandable connector arrangements form a closed loop in the circumferential direction around the barrel of a syringe held by the body, wherein the expandable connector arrangements are so configured that the body sections are movable between a non-retaining position and a retaining position.

The combination of syringe holder in accordance with the first aspect and a prefilled syringe forms part of a medical injector that may be configured for expelling one or more doses from the prefilled syringe.

For the syringe holder in accordance with the first aspect, due to the expandable connector arrangements, both the distal end and the proximal end of each body section are movable in radial direction individually from the other of the at least two body sections. This enables use of a tool for handling and operating the syringe holder to allow axial insertion of a syringe into the syringe holder while the needle shield is kept free from contact with the body sections of the syringe holder during axial insertion of the syringe into the syringe holder. Hence, the risk that the needle shield becomes moved relative to the barrel of the syringe, as the syringe is inserted into the syringe holder, will be reduced. This will reduce the risk that the sterility of the syringe needle becomes compromised.

The syringe holder may be so formed that each of the expandable connector arrangements interconnects respective longitudinally extending edges of neighbouring body sections.

Due to the expandable connector arrangements, the body sections and the expandable connector arrangements circumferentially form a closed loop when the body sections assume the retaining position. Even when the syringe holder is circumferentially expanded so that the body sections assume the non-retaining position the body sections and the expandable connector arrangements circumferentially form a closed loop.

In some embodiments, the syringe holder is formed as a single-piece component, i.e. wherein all of the at least two body sections are formed unitarily with the plurality of expandable connector arrangements. In some embodiments, the syringe holder forms a molded component, wherein the body sections and the expandable connector arrangements form a permanently closed loop. Hence the closed loop of the syringe holder is present even before the syringe is received within the syringe holder. The syringe holder may in some embodiments be made of a resiliently deformable material, such as a polymeric material.

The expandable connector arrangements are configured so that the closed loop is expandable to enable circumferential expansion of the closed loop and/or contractable to enable circumferential contraction of the closed loop.

The plurality of expandable connector arrangements may be formed to enable circumferential contraction of the body sections from the non-retaining position to the retaining position.

The syringe may be formed so that the body sections provide a contractive force on the barrel of a held syringe when the body sections are in the retaining position. Hence, with the body sections in the retaining position, the syringe may be held firmly within the syringe holder. This prevents rattling and provides superior protection for the syringe.

Also, in some embodiments, the plurality of expandable connector arrangements may be formed to enable circumferential expansion of the body sections from the retaining position to the non-retaining position.

Each body section may be formed to extend from said distal end with a shoulder section to a proximal end. The body sections of the syringe holder may be formed so as to extend along a substantial part of the cylindrical portion of a syringe. For example, the body sections may be formed to extend from the neck portion of a syringe along more than 50%, such as more than 60%, such as more than 70%, such as more than 80%, such as more than 90% of the length of the tubular portion of a held syringe. In some embodiments, the body sections of the syringe holder are formed to extend proximally from the neck portion along a substantial part of the tubular portion of the barrel of the syringe so that a free axial space larger than 1 mm, such as larger than 2 mm, such as larger than 3 mm between a proximal rim portion of the body sections and the finger flange is provided. In other embodiments, the body sections extend proximally from the neck portion of a held syringe so that a proximal portion of the body sections engage the finger flange so as to support the syringe flange, or even provide a gripping function to prevent the syringe from moving proximally relative to the syringe holder.

The individual body sections may be formed so as to provide rigid shell portions to accommodate the barrel of the syringe, wherein the body sections maintain a non-deformed state during insertion of the syringe into the syringe holder.

The expandable connector arrangements may be formed to enable the body sections to be movable radially so that the body sections are individually movable to assume a substantially parallel configuration in the retaining position and also to assume a substantially parallel configuration in the non-retaining position.

In certain embodiments each expandable connector arrangement is formed to comprise two or more linkage sections being arranged in a concertina configuration in the circumferential direction of the body of the syringe holder.

The linkage sections are in some embodiments formed as rigid linkage sections that are interconnected by hinges. The hinges that interconnect the linkage sections and/or the hinges that connect linkage sections with the body sections are in some embodiments formed as living hinges. Each of the hinges may provide for a swivelling movement around an axis parallel with the longitudinal axis of a held syringe.

In further embodiments, each concertina configuration may include more than two linkage sections, such as three, four or more. Still other embodiments may incorporate expandable connector arrangements which do not include rigid linkage sections interconnected by dedicated hinge sections. For example, the expandable connector arrangement may be provided as continuously deformable meandering or corrugated portions that allow the expandable connector arrangement to stretch or contract when forces are applied onto the syringe holder body.

In some embodiments, the concertina configurations may be formed so that the body sections move from the retaining position towards the non-retaining position when radially inwards directed forces are exerted onto the expandable connector arrangements. The syringe holder may be formed so that the body sections resiliently return to the retaining position when said forces are released.

In some embodiments the syringe holder is formed so that only a single expandable connector is located between the adjacent side portions of two neighbouring body sections. In such embodiments, the expandable connector arrangements may be formed so that the expandable connector includes longitudinally extending connectors that extend and axially overlap the barrel of a received syringe along a substantial portion of the length of the barrel, such as more than 40%, more that 50% or more than 70% of the length of the tubular part of the barrel.

In other embodiments, each expandable connector arrangement between any two neighbouring body sections are provided as two or more individual linkage sections, such as three or four individual linkage sections, disposed longitudinally at respective axial locations along the length of an inserted syringe.

In some embodiments, the syringe holder may be formed with two opposing body sections arranged symmetrically around a longitudinal axis. In such embodiment, each of the four longitudinal edge portions of the two body sections are interconnected to a neighbouring longitudinal edge portion by an expandable connector arrangement. In this way, for the two body section embodiments, two expandable connector arrangements are provided. The two expandable connector arrangements may both be arranged at the same particular axial location of the syringe holder, thus forming a pair of expandable connector arrangements. In embodiments wherein the expandable connector arrangements form connectors that only extend by a fraction of the axial length of the syringe holder, multiple pairs of expandable connectors may be arranged at different axial locations of the syringe holder, such as by having a pair arranged at the distal end of the syringe holder, and a pair arranged at the proximal end of the syringe holder.

In some embodiments, the linkage sections may be formed so that each individual linkage section only includes a single linkage beam between two neighbouring sections and wherein opposing ends of the linkage beam connect to a respective body section by means of a hinge. In such embodiments, each linkage beam may be formed so that it extends at an angle with respect to the circumferential direction when the body sections assume their retaining position. When the body sections assume their non-retaining position, the said angle will be reduced compared to when the body sections assume their retaining position. In such embodiments, the two body sections will move axially relative to each other as the body sections move from the non-retaining position to the retaining position, or vice versa.

In some embodiments each expandable connector arrangement arranged between longitudinal edge portions of any two neighbouring body sections are provided as at least one linkage section, wherein opposing ends of the linkage section connect to a respective body section by means of a hinge. The linkage section comprises a linkage section segment that extends inclined with an angle of inclination relative to the circumferential direction when the body sections assume their retaining position. As the linkage sections are hinged the body sections are movable axially relative to each other so that the body sections are forced to move radially as the body sections move axially relative to each other.

Said angle of inclination between the linkage section segment and the circumferential direction is increased as the body sections are moved from the non-retaining position to the retaining position as the body sections undergoes relative axial movement.

In some embodiments, when the body sections of the syringe holder assume the retaining position, the said angle of inclination between the linkage section and the circumferential directions is more than 10 deg., such as more than 20 deg., or more than 30 deg. In some embodiments, when the body sections of the syringe holder assume the retaining position, the said angle of inclination between the linkage section and the circumferential directions is within the interval 40-50 deg.

In some embodiments, when the body sections assume the retaining position, the linkage sections extend helically around a syringe held by the syringe holder.

In some embodiments the syringe holder is provided so that each expandable connector arrangement between longitudinal edge portions of any two neighbouring body sections are provided as a plurality of individual linkage sections disposed longitudinally at respective axial locations along the body sections.

In some embodiments, the plurality of individual linkage sections are so configured that when the body sections move axially relative to each other, a distal portion of the body sections move radially relative to each other and a proximal portion of the body sections move radially relative to each other as the body sections move axially relative to each other.

In some embodiments, the plurality of individual linkage sections between any two neighbouring body sections is configured as a parallelogram configuration.

In a second aspect, the present invention relates to a medical injector comprising a syringe holder as defined in connection with the first aspect, and further comprising a syringe having a barrel and a needle shield covering a needle of the syringe, wherein a circumferential gap is provided between the barrel of the syringe and the needle shield, wherein the barrel of the syringe is received in the body, and wherein the shoulder sections are positioned within the circumferential gap.

The medical injector may further comprise an outer housing wherein the outer housing comprises one or more interface geometries engaging interface geometries of the syringe holder for positioning the syringe holder relative to the outer housing.

In such medical injector the syringe holder may be provided so that each expandable connector arrangement comprises two or more linkage sections being arranged in a concertina configuration in the circumferential direction of the body of the syringe holder. One or more interface geometries of the outer housing may be formed to comprise a clamping structure configured to engage cooperating clamping surfaces of the expandable connector arrangements to clamp the two or more linkage sections of the concertina configuration towards each other so that the body sections are retained in the retaining position.

In some embodiments, the barrel of the syringe comprises a proximally arranged finger flange extending radially from the wall of the barrel, wherein the finger flange includes a proximally facing surface and a distally facing surface. The syringe holder may be so configured that when the barrel of the syringe is received in the body of the syringe holder so that the shoulder sections are positioned within the circumferential gap the distally facing surface of the finger flange is spaced axially from the syringe body.

The medical injector may in some embodiments be configured as an autoinjector. In other embodiments, the medical injector may be configured as a manual injector. In some embodiments, the medical injector is configured as a disposable injector wherein the prefilled syringe is permanently held within a housing defined by the medical injector, i.e. in a manner preventing removal of the held syringe from the housing.

In a third aspect, the invention relates to a method of forming a medical injector assembly comprising a syringe holder as defined in accordance with any of the variants described above in relation to the first and second aspects. The method comprises the steps of:

a) providing the syringe comprising a barrel, a needle attached to the distal end of the barrel and a needle shield covering the needle of the syringe, wherein a circumferential gap is provided between the barrel and the needle shield,
b) providing the syringe holder according to the first aspect with the body sections assuming the non-retaining position,
c) placing the syringe in the syringe holder,
d) moving the body sections from the non-retaining position to the retaining position such that the shoulder sections are received within the circumferential gap between the barrel of the syringe and a needle shield covering a needle of the syringe to prevent the syringe from moving distally (D) relative to the syringe holder.

In some embodiments, the method step b) further comprises the step of positioning the syringe holder relative to a tool comprising at least first and second tool parts. The method step d) further comprises the steps of engaging respective ones of the at least first and second tool parts with respective ones of the at least at least two body sections, and positioning the at least first and second tool parts relative to each other thereby moving the body sections from the non-retaining position to the retaining position.

The method step b) may further comprise, prior to step c), the step of using the tool parts for engaging and moving the body sections from the retaining position to the non-retaining position.

In other embodiments, the method step b) further comprises the steps of positioning the syringe holder relative to a tool comprising at least first and second tool parts, engaging respective ones of the at least first and second tool parts with respective ones of the at least at least two body sections and positioning the at least first and second tool parts relative to each other thereby moving the body sections to the non-retaining position.

In particular forms wherein the syringe holder comprises linkage section segments having an inclination relative to the circumferential direction, the step or steps of moving the body sections from the retaining position to the non-retaining position or vice versa comprises the step of axially moving the body sections relative to each other so that the body sections move radially relative to each other.

In still further embodiments, the method, subsequent to step d), further comprises the steps of:

e) providing an outer housing, wherein the outer housing comprises one or more interface geometries, f) inserting the syringe holder with the syringe held by the syringe holder relative to the outer housing so that the interface geometries of the housing engage the body of the syringe holder for maintaining the body sections in the retaining position.

In a fourth aspect, the present invention relates to a syringe holder comprising:

a body extending along a central longitudinal axis and adapted to receive the barrel of a syringe, wherein the body includes at least two body sections disposed around the central longitudinal axis, the body sections having distal ends with shoulder sections adapted for being received in a circumferential gap between the barrel of the syringe and a needle shield covering a needle of the syringe to retain the syringe so as to prevent the syringe from moving distally (D) relative to the syringe holder, wherein the body sections are resiliently movable in radial direction so that the shoulder sections are positionable in a radially outwards position and a radially inwards position wherein, when the shoulder sections assume the radially outwards position the needle shield attached to a syringe may be moved to pass axially in between the shoulder sections, and wherein when the shoulder sections assume the radially inwards position the shoulder sections are positioned and received in the circumferential gap to retain the syringe, wherein the body sections each comprise a radially outwards facing spring seat for cooperating with a helical compression spring, and wherein when said helical compression spring is arranged in engagement with said spring seat of the body sections, one or more windings of the helical compression spring encircle the body sections to prevent the shoulder sections from moving away from the radial inwards position.

In some embodiments, the syringe holder according to the fourth aspect is provided as part of a syringe holder assembly, wherein the syringe holder assembly further comprises a syringe with a needle shield attached covering the needle of the syringe and with the circumferential gap between the barrel of the syringe and the needle shield being arranged in engaging relationship with the shoulder sections of the barrel of the syringe.

In further embodiments, the syringe holder assembly further comprises a helical compression spring arranged in engagement with the spring seat of the body sections, the helical compression spring providing a radially inwards clamping force on the body sections.

In further embodiments, the syringe holder assembly further comprises a needle shroud, wherein the needle shroud is translationally movable from a collapsed proximal position where the needle of the syringe protrudes through the needle shroud to an extended distal position where the needle shroud covers the needle, and wherein the helical compression spring is arranged axially between the syringe holder and the needle shroud to provide a biasing force acting to urge the needle shroud towards the distal extended position.

In still further embodiments, the helical compression spring includes at least one portion having open windings and at least one portion having closed windings, and wherein said at least one portion having closed windings are arranged in engagement with the body sections so that a plurality of windings of the at least one portion having closed windings of the helical compression spring provides a radially inwards clamping force on the body sections.

As used herein, the term "drug" is meant to encompass any drug-containing flowable medicine or combinations of separately held plurality of drug-containing flowable medicines capable of being passed through a delivery means such as a cannula or hollow needle in a controlled manner, such as a liquid, solution, gel or fine suspension.

BRIEF DESCRIPTION OF DRAWINGS

In the following the invention will be further described with reference to the drawings, wherein.

Figure 1:
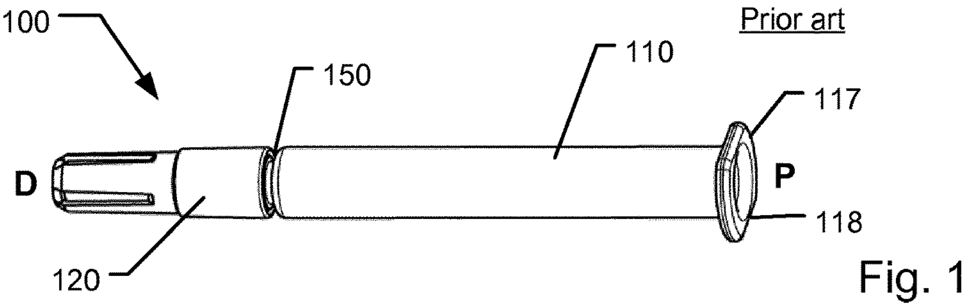
FIG. 1 shows a perspective side view of a prior art standard prefilled syringe 100.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DESCRIPTION

In the context of the present disclosure it may be convenient to define that the term "distal end" in the appended figures is meant to refer to the end of the injection device which usually carries the injection needle whereas the term "proximal end" is meant to refer to the opposite end of the injection device pointing away from the injection needle. The shown figures are schematical representations for which reason the configuration of the different structures as well as the relative dimensions are intended to serve illustrative purposes only.

FIG. 1 shows a standard prefilled syringe (PFS) as widely used in industry. Reference is further made to FIG. 4*b* which provides a cross-sectional side view of a prefilled syringe as part of an assembly which additionally comprises a syringe holder according to a second embodiment. The syringe 100 comprises a tubular barrel 110 having a neck portion 115 located distally wherein the neck portion 115 has a reduced diameter compared to the diameter of the barrel 100. An injection needle 130 is mounted to the neck portion 115 and a removable cap provided in the form of a rigid needle shield (RNS) 120 is attached to the neck 115 so that the needle shield 120 sealingly and sterilely seals off the needle 130. Internally in the barrel 110 a slideably arranged piston 140 is arranged. A drug may be accommodated within the barrel between the piston 140 and the needle 130. Although the shown syringe only incorporates a single piston 140, other configurations may incorporate multiple pistons for accommodation and expelling of one or more drugs, including drugs to be reconstituted before administration. The syringe 100 depicted in FIG. 1 further includes a proximally arranged finger flange 117 extending radially from the wall of the barrel 110, wherein the flange includes a couple of alignment features 118. For the shown syringe, a circumferential gap 150 exists between the barrel 110 of the syringe 100 and the needle shield 120 covering the needle 130.

Figure 2A:
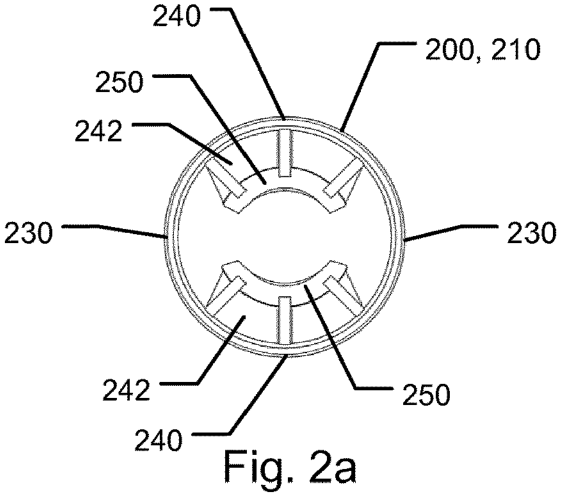
FIG. 2*a* shows a cross sectional front view of a first embodiment of a syringe holder 200, wherein the syringe holder is shown in a non-biased state.
Figure 2B:
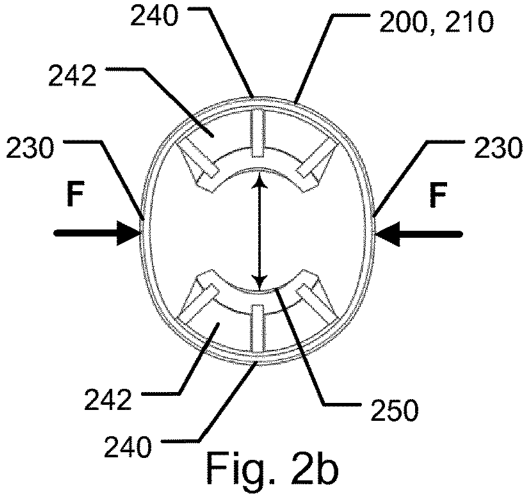
FIG. 2*b* shows the syringe holder 200 of FIG. 2*a* in a similar view, but wherein the syringe holder is depicted in a biased state during assembly operations.
Figure 3A:
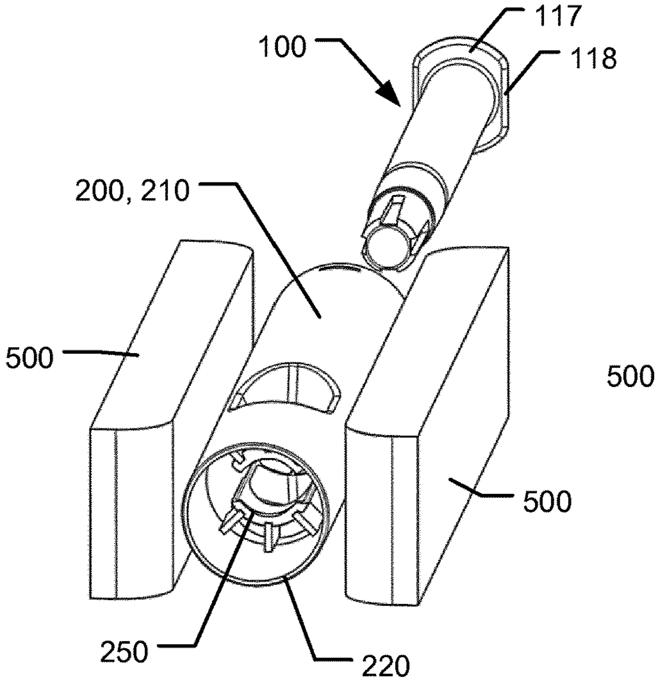
FIGS. 3*a*-3*f* depict a series of perspective front views of the syringe holder 200 of FIG. 2*a* together with a syringe 100 and a tool 500, the series of views representing different states during assembly operations.
Figure 3B:
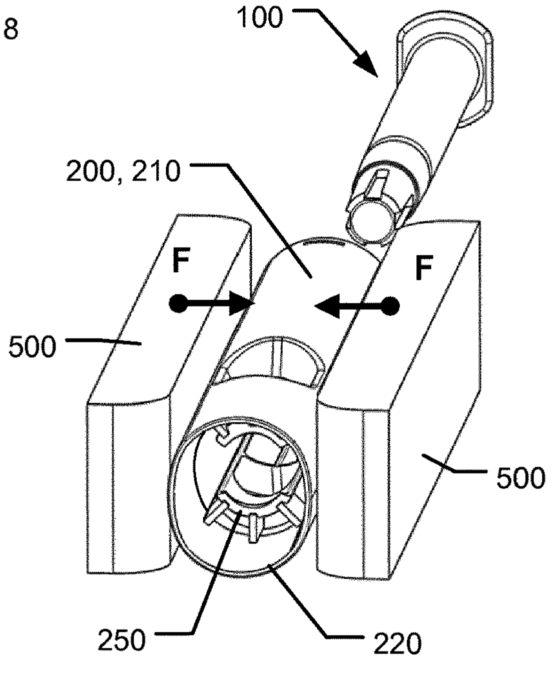
Figure 3C:
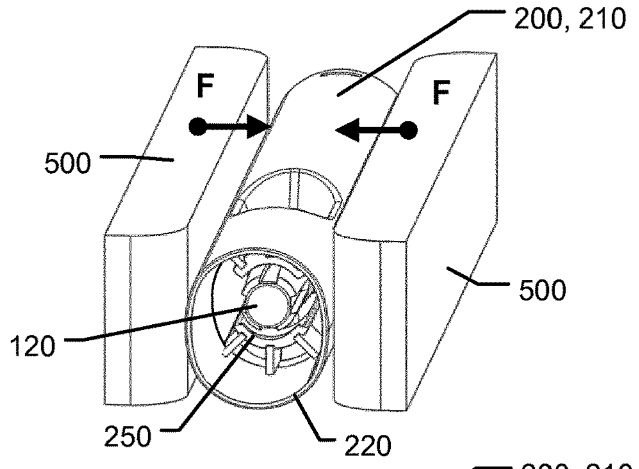
Figure 3D:
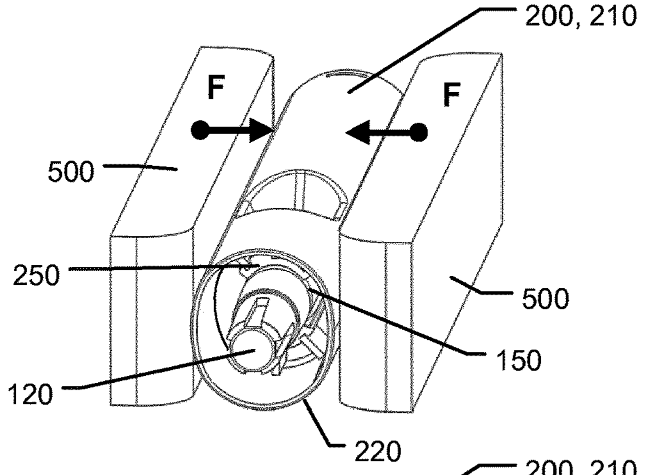

FIGS. 2*a* and 2*b* schematically show a cross sectional view of a syringe holder 200 of a first embodiment with each figure depicting the syringe holder in one of two different states. The syringe holder 200 is intended to accommodate a syringe 100 of the type shown in FIG. 1. The syringe holder 200 is also depicted in FIGS. 3*a* and 3*b* showing perspective front views corresponding to the states shown in FIGS. 2*a* and 2*b*. Also shown in FIGS. 3*a* and 3*b* is a syringe 100 intended to be inserted into the syringe holder 200.

The syringe holder 200 includes a body 210 generally formed as tubular outer shell with a distal rim portion 220 arranged pointing in the distal direction adjacent the needle 130 of a held syringe 100. The tubular outer wall of body 210 includes a proximal opening arranged to receive syringe 100. The tubular outer wall includes two opposing longitudinally extending body sections 240 that are interconnected on each side by longitudinal extending segments 230, wherein the segments each form an expandable connector arrangement. In order to retain the syringe 100 inside syringe holder 200, the body sections 240 of the outer wall of body 210 comprises, on a radially facing inner surface, a pair of support structures 242 with opposed shoulder sections 250 pointing radially inwards at an axial location near the distal rim portion 220 of the tubular outer wall of body 210. The two support structures 242 are symmetrically arranged at the same axial position inside the tubular outer wall and with the two support structures 242 spaced apart leaving a free space in the circumferential direction between the two support structures 242. Each of the shoulder sections 250 define an arcuate surface portion shaped for being received into the gap 150 between the barrel 110 and the needle shield 120 of a held syringe 100, i.e. so that the shoulder sections engages the neck portion 115 of barrel 110. In the shown embodiment, the syringe holder 200 includes two opposed shoulder sections 250. However, other embodiments may include more than two, such as three or four shoulder sections. The shoulder sections 250 are movable between a retaining position (shown in FIG. 2*a*) and a non-retaining position (FIG. 2*b*).

The view shown in FIG. 2*b* depicts the syringe holder 200 in a biased state where externally applied opposing forces F are applied radially inwards on the segments 230 of the body 210 at the locations indicated in the figure. In FIG. 2*a* the syringe holder 200 is shown in an unbiased state where the forces F have been released and the tubular shell of body 210 assumes a circular configuration.

FIGS. 3*a*-3*f* show a series of perspective front views of the syringe holder 200 together with a syringe 100 and a tool 500, the series of views representing different states during assembly operations. The tool 500 is configured to apply the forces F onto segments 230 during insertion of the syringe 100 into the syringe holder 200. The external forces F are exerted on each side of the body 210 along the axis of symmetry between the support structures 242. As a result segments 230 of the tubular shell is deformed locally inwards at locations where the tool 500 presses inwards resulting in the body sections 240 of the body 210 are being forced radially outwards. Hence the tubular shell of body 210 assumes an oval configuration with the support structures 242 being spread apart.

Figure 3E:
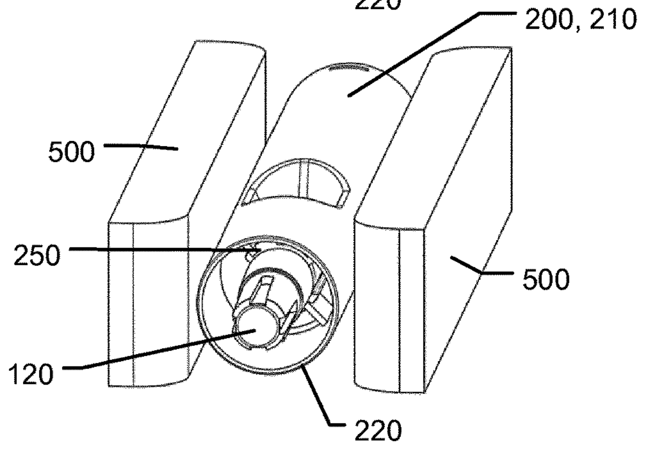
Figure 3F:
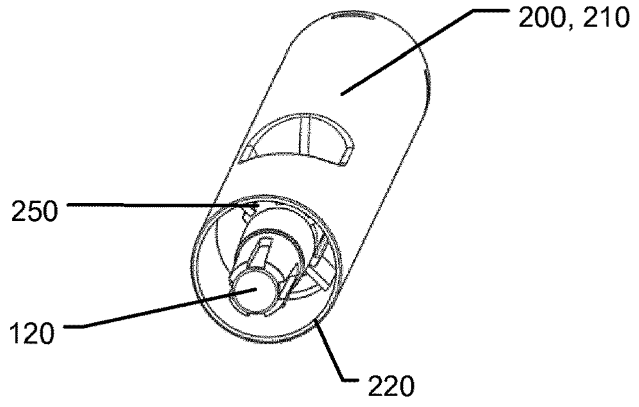

As shown in FIGS. 2*b* and 3*b*, the distance between the shoulder sections 250 is increased as the forces F are applied by the tool 500. This leaves room for the syringe 100, with the needle shield 120 attached, to be inserted axially from the proximal end of the body 210 (see FIG. 3*c*). By controlling the axial insertion of the syringe 100 into the syringe holder 200 the syringe may be positioned so that the gap 150 of the syringe becomes located axially aligned with the shoulder sections 250 (see FIG. 3*d*). Upon discontinuation of the forces F, as shown in FIG. 3*e*, the tubular shell of body 210 again assumes a circular configuration, thus moving the shoulder sections 250 radially towards each other establishing a firm grip between the shoulder sections 250 and the neck portion 115 of the syringe with a proximally facing surface of the shoulder sections 250 engaging the barrel 110 of the syringe 100. FIG. 3*f* shows the assembly formed by syringe 100 and syringe holder 200 after the assembly has been removed from the tool 500 wherein the syringe 100 is being prevented from moving distally relative to the syringe holder 200.

In the shown embodiment, the syringe holder 210 is made from a material which is resiliently deformable and which allows the tubular wall of body 210 and the shoulder sections 250 to return to the original shape and position as the forces F are released.

Alternatively, the syringe holder 210 may be made from a material which is deformable from the shape shown in FIG. 2*b* and into the shape shown in FIG. 2*a*, for example by applying forces radially inwards on each side of the tubular wall at body sections 240 that hold the support structures 242. After insertion of the syringe into the syringe holder, the sections including the shoulder sections of the syringe holder may be forced to maintain the retaining position by means of an external fixing means. Alternatively, in case the syringe holder is made from a plastically deformable material, the plastic deformation may be utilized to maintain the syringe holder with the shoulder sections in the retaining position after the syringe has been properly inserted.

In the embodiment shown, the syringe holder 200 is intended to form an outer housing of a medical injector. The medical injector may further include an expelling mechanism for expelling one or more doses of a drug contained within the syringe 100 as well as various other components for providing different functions. In the embodiment shown, the syringe is thus held directly by the outer housing. Hence, the design dispenses with the requirement of having further dedicated components for holding the syringe within the outer housing, e.g. preventing the syringe from uncontrolled movements in the distal direction relative to the outer housing.

In other not shown embodiments, a syringe holder 200, provided in accordance with the general principle shown in FIGS. 2*a* through 3*f*, may be designed to form a dedicated syringe holder intended to define an internal component of an injection device. The syringe holder in combination with a syringe held by the syringe holder may thus define a sub-assembly which is intended to be inserted into a separately formed outer housing, either in an axially fixed or in an axially slideable relationship.

Figure 4A:
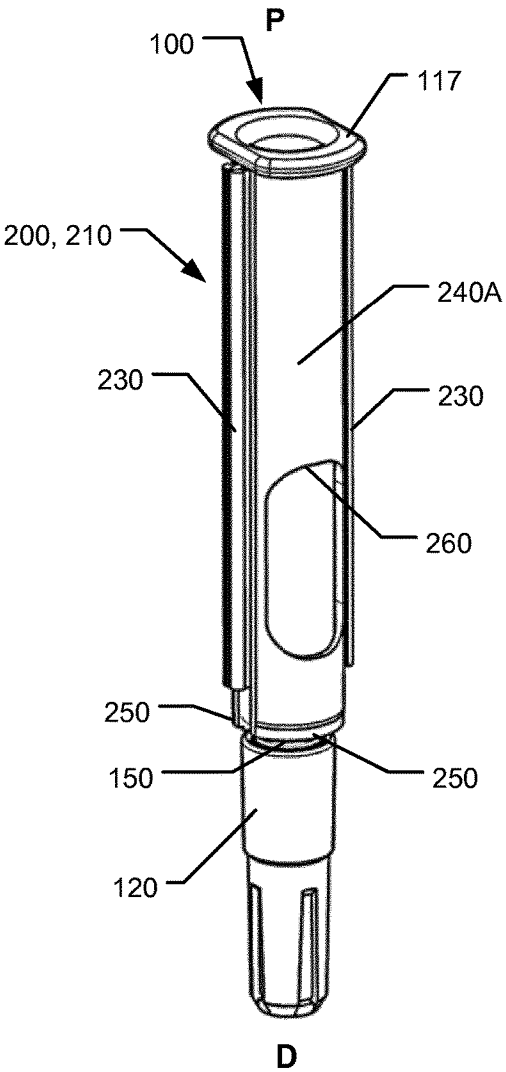
FIG. 4*a* shows a perspective side view of an assembly of a syringe and a syringe holder of a second embodiment.

FIG. 4*a* shows a perspective side view of an assembly of a syringe holder 200 of a second embodiment in combination with a syringe 100, the figure depicting the state where the syringe is held in a retaining manner by the syringe holder. FIG. 4*b* depicts a planar side view of the assembly in a first cross sectional view whereas FIG. 4*c* shows a cross sectional view orthogonally to the view shown in FIG. 4*b*. A cross sectional axial view of the syringe holder is provided in FIG. 4*d*. The shown cross section is provided through a window area of the syringe holder 200, the window defined by cut-outs 260.

Figure 7A:
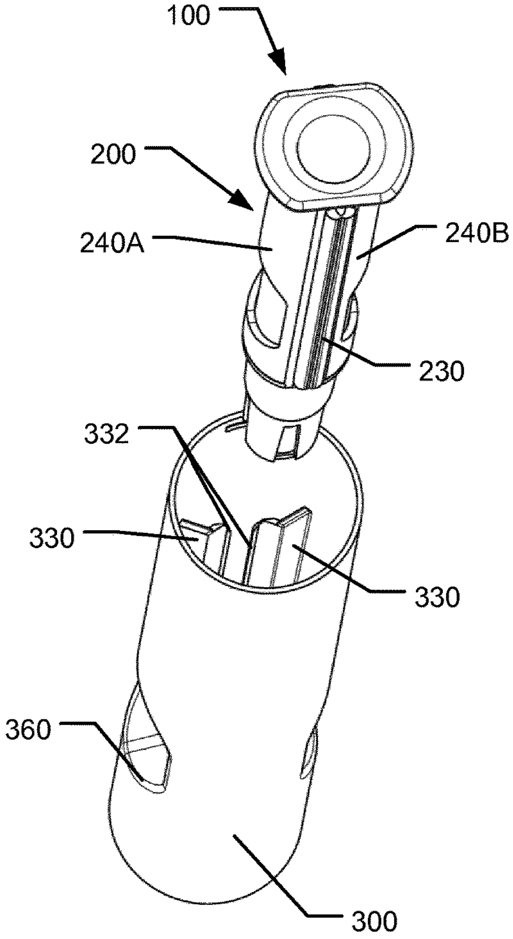
FIG. 7*a* shows a perspective rear view of a syringe holder assembly 100/200 of the second embodiment together with an outer housing 300 of an injection device in a state prior to insertion.

As indicated in FIG. 7*a*, the syringe holder 200 of the second embodiment is intended to form a dedicated syringe holder intended to define an internal component of an injection device. The syringe holder 200 in combination with a syringe 100 held by the syringe holder 200 may thus define a sub-assembly which is intended to be inserted into a separately formed outer housing 300, either in an axially fixed or in an axially slideable relationship. However, although not shown, the general principle may also be utilized in alternative embodiments where the syringe holder forms an outer housing of a medical injector.

The syringe holder 200 includes a body 210 formed as a generally tubular outer shell extending along a central longitudinal axis and shaped to define a cylindrical open space suitable to receive the barrel 110 of a held syringe 100. The body 210 includes two longitudinally extending body sections 240A and 240B symmetrically arranged in an opposed manner around the central longitudinal axis. Each body section 240A/240B has a distal end with a shoulder section 250 adapted to engage a circumferential gap 150 between the barrel 110 of the syringe 100 and a needle shield 120 covering the needle 130 of the syringe. In the state shown the shoulder sections 250 assume a retaining position wherein a proximally facing surface of each shoulder section 250 engages the neck portion 115 of the barrel 110 thus preventing the syringe 100 from moving in a distal direction (D) relative to the syringe holder 200. Each of the body sections 240A/240B define two longitudinal extending side edges running in parallel from the shoulder sections arranged at the distal end to a proximal end of the body 210. In the shown embodiment, when a syringe 100 is held by the syringe holder 200, the proximal ends of body sections 240A/240B are located a distance from the finger flange 117 of the syringe 100.

The two body sections 240A/240B are individually movable relative to each other in a radial direction by means of expandable connectors 230 that connect the two body sections 240A/240B at longitudinal extending edges thereof. In the shown embodiment adjacent longitudinal extending edges of the two body sections 240A/240B are interconnected by an expandable connector 230 that extends along a substantial portion of the barrel 110 of a held syringe. As an expandable connector 230 is arranged at each longitudinal extending edge of the body 210 the syringe holder forms a closed loop in the circumferential direction to circumscribe the barrel of a held syringe. However, due to the expandable connectors 230, the body 210 is circumferentially contractible so as to move the two body sections 240A/240B, and thus the shoulder sections 250, from the non-retaining position into the retaining position. In the shown embodiment, the body 210 is circumferentially expandable and contractible. Hence, the two body sections 240A/240B are reversibly movable from the non-retaining position into the retaining position. In the second embodiment, the shoulder sections 250 assume the retaining position shown in FIGS. 4*a*-4*d* when the syringe holder 200 assumes an unbiased state. However, in other embodiments, the shoulder sections 250 may assume the non-retaining position when the syringe holder 200 assumes an unbiased state. In still other embodiments, the shoulder sections may assume an intermediate position between the retaining position and the non-retaining position when the syringe holder is in an unbiased state.

Figure 4D:
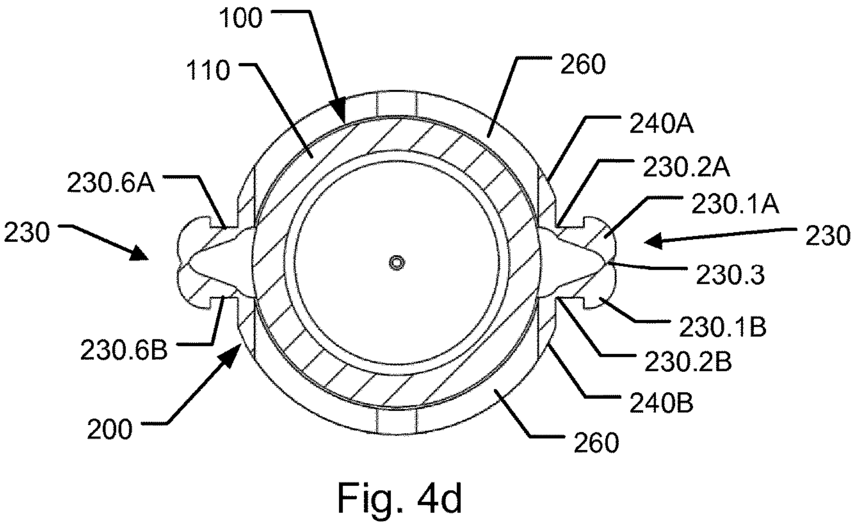
FIG. 4*d* is a cross sectional axial view of the syringe holder 200 of the second embodiment at an axial location through a window portion of the syringe holder.
Figure 4B:
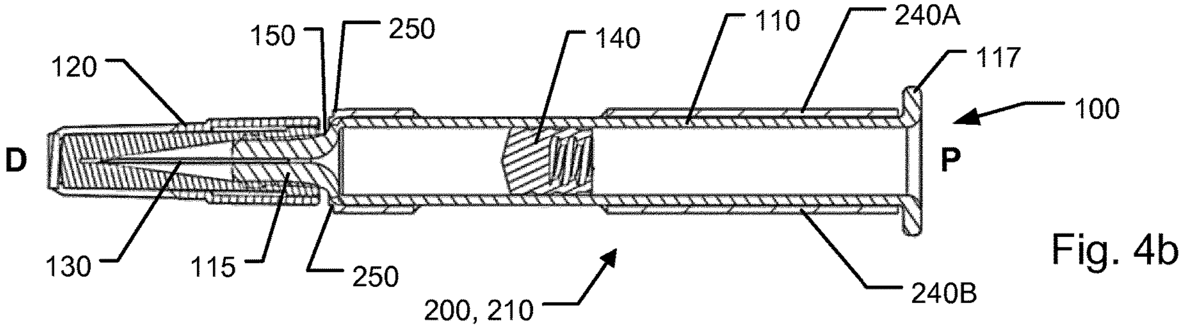
FIGS. 4*b* and 4*c* are first and second cross sectional side views of the syringe holder 200 of the second embodiment, wherein the view in FIG. 4*c* is depicted 90 deg. relative to the view shown in FIG. 4*b*.
Figure 4C:
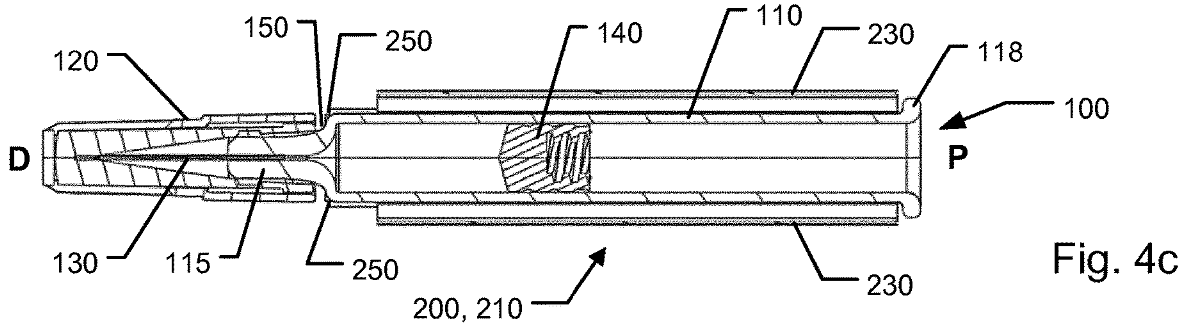

As most clearly viewable from FIG. 4*d* the expandable connector arrangements 230 each comprises a pair of linkages that includes hinges at their ends. In the shown embodiment, the expandable connector arrangement 230 comprises first and second linkage sections 230.1A and 230.1B that are connected relative to each other by means of a living hinge 230.3. The first linkage section 230.1A is further linked to a first (upper) body section 240A by a living hinge 230.2A whereas the second linkage section 230.1B is further linked to a second (lower) body section 240B by a living hinge 230.2B. All said living hinges allow for swivelling movements in the plane of the drawing, i.e. orthogonally to the central longitudinal axis that runs through a syringe 100 inserted into the syringe holder 200. The shown design of the expandable connector 230 allows the body sections 240A/240B to be moved radially relative to each other by circumferentially expanding the syringe holder body.

In the shown embodiment, the linkage configuration is provided forming a concertina configuration in the circumferential direction around the body 210 by means of two linkage sections 230.1A and 230.1B. However, other embodiments may include more than two linkage sections. Still other embodiments may incorporate expandable connector arrangements of other designs which do not include linkages interconnected by dedicated hinge sections. For example, the expandable connector arrangement may be provided as continuously deformable meandering or corrugated portions that allow the expandable connector arrangement to stretch or contract when a force is applied.

Also, in other embodiments, the design of the expandable connector arrangements 230 may be formed differently. For example, a single continuous linkage configuration shown in FIG. 4*a* that connects the two body sections 240 may be replaced by a series of individual connectors distributed at different axial positions along the length of the barrel 110 of a held syringe 100.

In the shown embodiment, the body 210 is provided by two opposing body sections that, wherein the neighbouring longitudinal edges of the respective body sections are interconnected by expandable connector arrangements 230 so that two expandable connector arrangements 230 are arranged in an opposed manner. In other embodiments, the number of body sections may be provided as three or more sections distributed around the circumference of a held syringe, where longitudinal edges of neighbouring body sections are interconnected by an expandable connector arrangement.

Figure 5A:
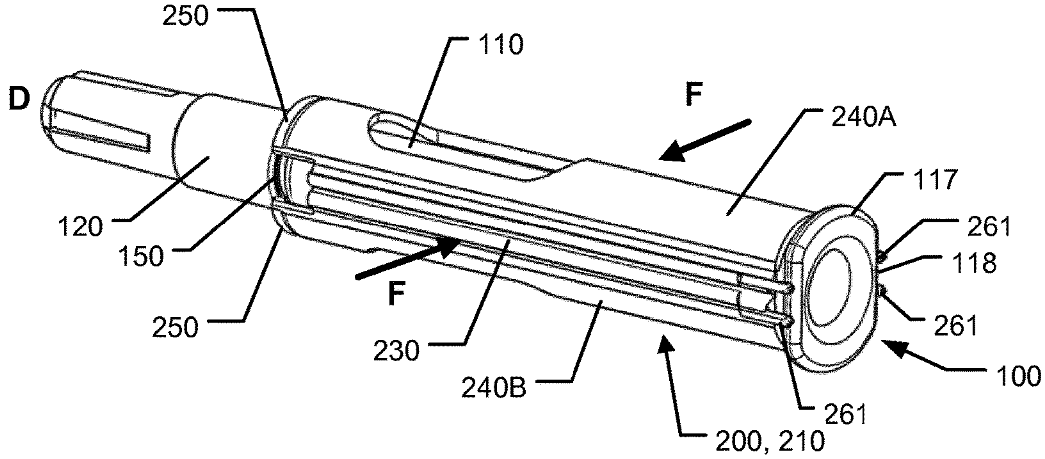
FIGS. 5*a* and 5*b* show perspective views of an assembly of a syringe 100 and a syringe holder 200 of a third embodiment, FIGS. 5*a* and 5*b* respectively showing the syringe holder in a biased state and in a non-biased state during assembly.
Figure 5B:
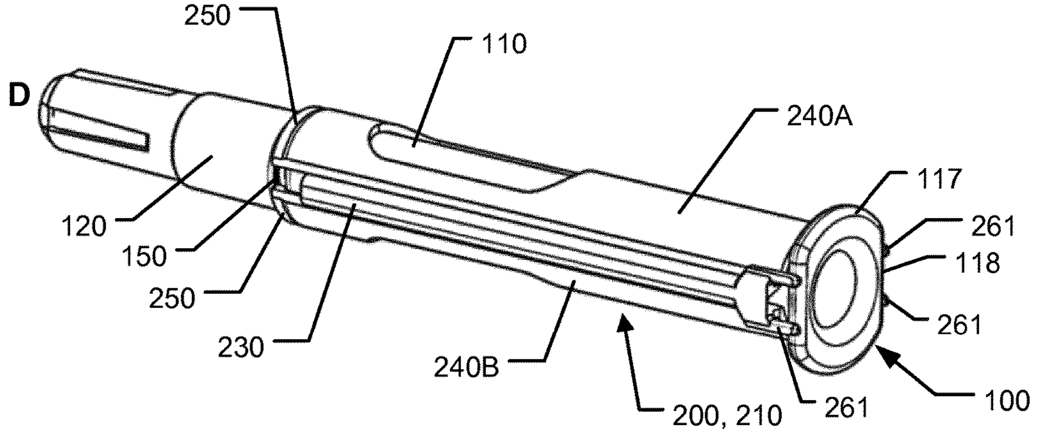

FIGS. 5*a* and 5*b* show a third embodiment of a syringe holder 200 in combination with a held syringe 100 inserted axially so that the shoulder sections 250 axially aligns with the gap 150 formed between the barrel 110 and the needle shield 120. The depicted syringe holder 200 generally corresponds to the syringe holder of the second embodiment but a plurality of alignment features 261 are formed to protrude in the proximal direction from the proximal end of the linkage sections 230.1A and 230.1B. Alignment features 261 form guiding surfaces that may be used to rotationally align the syringe 100 relative to the syringe holder 200 by cooperating with the alignment features 118 formed on finger flange 117 of the syringe.

FIG. 5*a* shows the syringe holder 200 in a biased state where externally applied opposing forces (F), provided by a tool arrangement, are applied radially inwards on the expandable connector arrangements 230 at locations near the living hinge 230.3. The applied forces make the body sections 240A/240B move radially outwards which means, as evident in FIG. 5*a*, that a gap between the barrel 110 and the inner surface of body sections 240A/240B is formed, and in that the shoulder sections 250 are positioned radially outside the gap 150. Due to the applied forces the sections 240A/240B are in the non-retaining position which has allowed the axial insertion of the syringe into the syringe holder.

FIG. 5*b* shows the syringe holder 200 in an unbiased state where the radial inwards forces (F) previously applied have ceased. As seen in the figure, the above mentioned gap between the barrel 110 and the inner surface of body sections 240A/240B has disappeared and the shoulder sections 250 are positioned radially inside the gap 150 formed between the barrel 110 and the needle shield 120. In this state the syringe is prevented from moving distally due to the shoulder sections 250 will engage the neck portion 115 of the barrel 110 and block distal movement.

FIGS. 6*a*-6*f* show a series of perspective side views of the syringe holder 200 according to the second embodiment together with a syringe 100 and a tool arrangement 500, the series of views schematically providing a representation of the various states during assembly operations. The tool 500 is configured to apply the forces F onto the expandable connector arrangements 230 during insertion of the syringe 100 into the syringe holder 200.

Figure 6A:
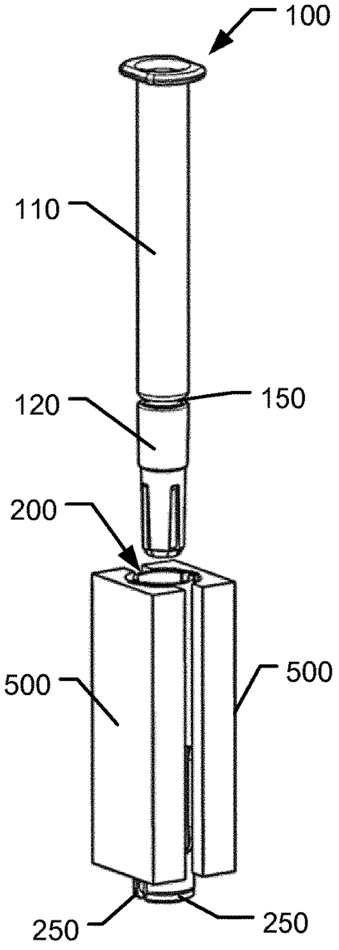
FIGS. 6*a*-6*f* depict a series of perspective views of the syringe holder 200 of FIG. 4*a* together with a syringe 100 and a tool arrangement 500, the series of views representing different states during assembly operations.
Figure 6B:
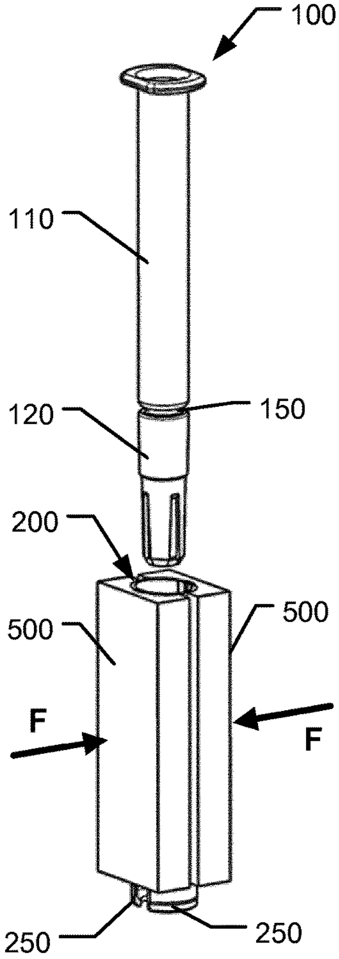
Figure 6C:
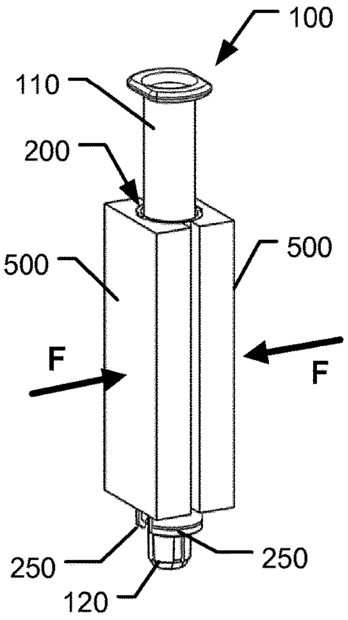
Figure 6D:
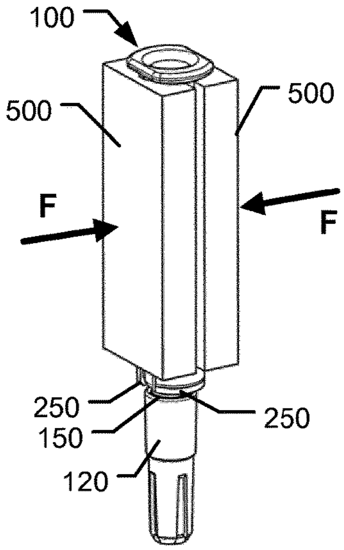
Figure 6E:
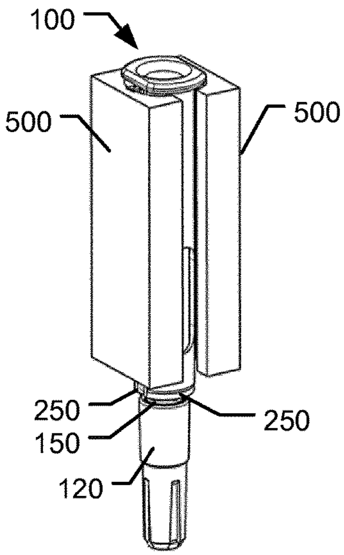
Figure 6F:
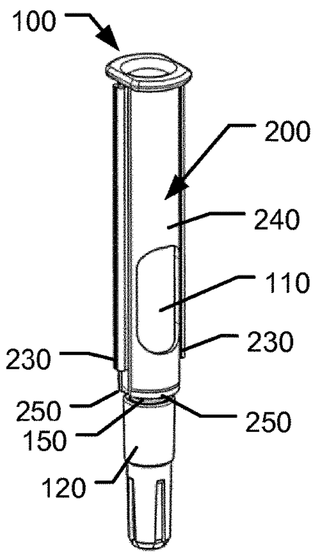

Prior to the state shown in FIG. 6*a*, the syringe holder 200 has been inserted axially into the tool 500. In FIG. 6*b* two gripping parts of tool 500 have been moved slightly towards each other in a direction orthogonally to the central longitudinal axis of the syringe holder 200, i.e. in a direction along an axis running through the two living hinges 230.3. As shown in FIG. 6*b*, the distance between the shoulder sections 250 has increased as a result of the forces (F) being applied by the gripping parts of tool 500. This leaves room for the syringe 100, with the needle shield 120 attached, to be inserted axially from the proximal end of the body 210 (see FIG. 6*c*). By controlling the axial insertion of the syringe 100 into the syringe holder 200 the syringe may be positioned so that the gap 150 of the syringe becomes located axially aligned with the shoulder sections 250 (see FIG. 6*d*). As shown in FIG. 6*e*, upon discontinuation of the applied forces F, i.e. by returning the gripping parts of tool 500 to the initial position, the tubular shell of body 210 again assumes the unbiased state where the shoulder sections 250 assume their retaining position. The shoulder sections 250 have thus been moved radially towards each other establishing a firm grip between the shoulder sections 250 and the neck portion 115 of the syringe with a proximally facing surface of the shoulder sections 250 engaging a shoulder section of the barrel 110 of syringe 100. FIG. 6*f* shows the assembly formed by syringe 100 and syringe holder 200 after the assembly has been removed from the tool 500. In the assembly 100/200, the syringe 100 is prevented from moving distally relative to the syringe holder 200.

The assembly 100/200 may be used in combination with other components forming part of a medical injector assembly. As shown in FIG. 7*a*, and further in FIGS. 7*b*-7*d*, the syringe and syringe holder assembly 100/200 may be inserted into a separately formed outer housing 300. The assembly formed by the outer housing, the syringe holder and the syringe, will optionally be combined with additional components, to form a medical injector, such as an autoinjector. The shown outer housing 300 comprises a plurality of interface geometries that protrude radially inwards from an outer shell portion 310 of the housing 330, the interface geometries being configured for engaging a set of cooperating interface geometries of the syringe holder 200.

Figure 7B:
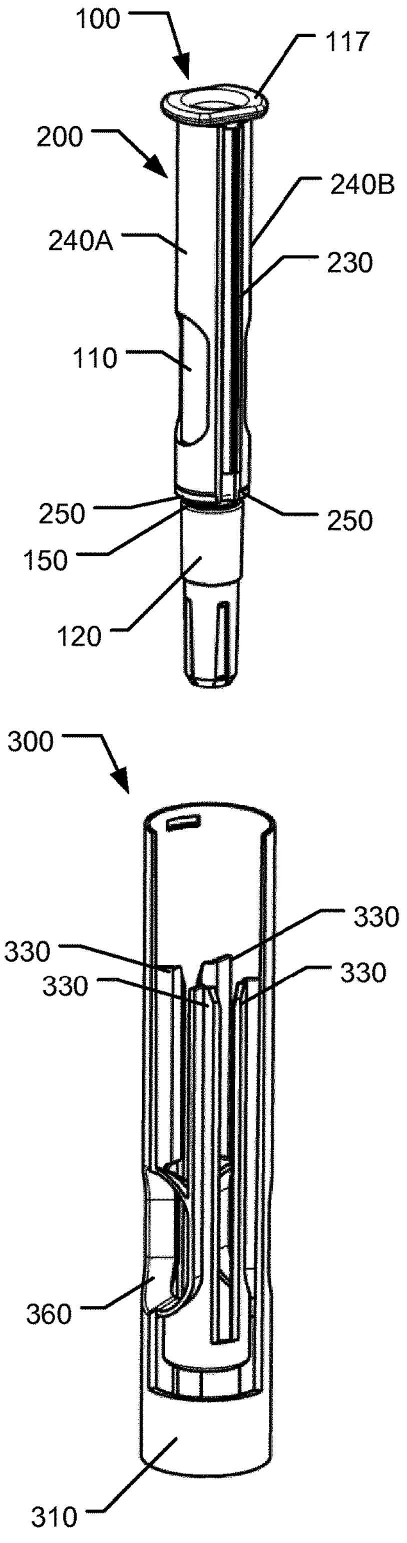
FIG. 7*b*-7*d* depict a series of perspective side views of the components shown in FIG. 7*a*, the series of views representing different states during insertion of the syringe and syringe holder assembly 100/200 into the outer housing 300.
Figure 7C:
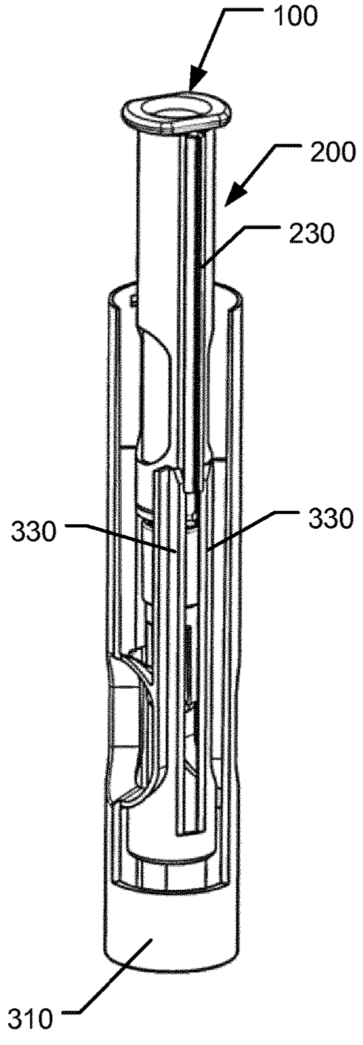
Figure 7D:
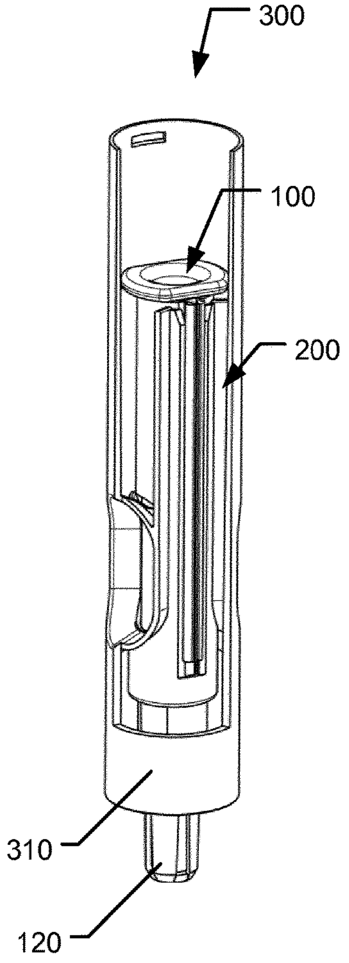

As shown in FIG. 7*b*, the interface geometries of the outer housing 300 include four separate guides 330 each of which are formed to extend in the longitudinal direction in parallel with the central longitudinal axis. Further not shown interface geometries may be provided for controlling the axial position of the syringe and syringe holder assembly 100/200 inside the outer housing.

In the shown embodiment, the four guides 330 are arranged pairwise to define two clamping structures 332 (see FIG. 7*a*). Each pair of guides 330 is configured to engage cooperating clamping surfaces 230.6A/230.6B of one of the expandable connector arrangements 230 of the syringe holder, cf. FIG. 4*d*. In the shown embodiment, when the syringe and syringe holder assembly 100/200 is inserted in the distal direction through a proximal opening of the outer housing 300, each of the clamping structure 332 exerts a clamping force on the two linkage sections 230.1A, 230.1B of the respective concertina configuration, urging the two linkage sections towards each other so that the two body sections 240A/240B of the syringe holder 200 are retained with the shoulder sections 250 in the retaining position. Hence, the two body sections 240A/240B are prevented from being moved away from each other by the cooperation with the outer housing and are fixedly positioned with the shoulder sections 250 in the retaining position. This state is maintained even when forces are applied onto the syringe in the distal direction, such as typically occurring during use of the medical injector, e.g. during administration wherein a distally directed force is exerted on the slideable piston 140 inside the syringe 100, or upon an impact which may be caused by accidentally dropping the device onto a hard surface.

As shown in the drawings the outer housing 300 may be formed to define window openings 360 which align with the window openings 260 of the syringe holder 200 when the syringe and syringe holder assembly 100/200 has been properly inserted into outer housing 300. This will enable the user to visually inspect the drug contained in the syringe.

Figure 8A:
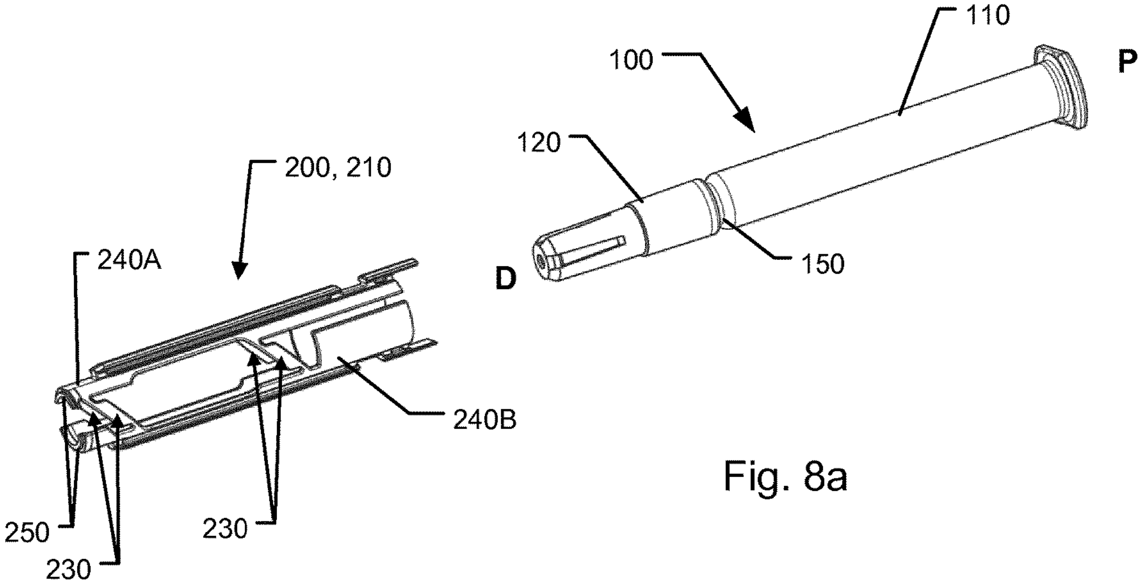
FIGS. 8*a* and 8*b* show perspective views of a syringe 100 and a syringe holder 200 of a fourth embodiment, FIGS. 8*a* and 8*b* respectively showing the syringe holder in a biased state and in a non-biased state before assembly.
Figure 8B:
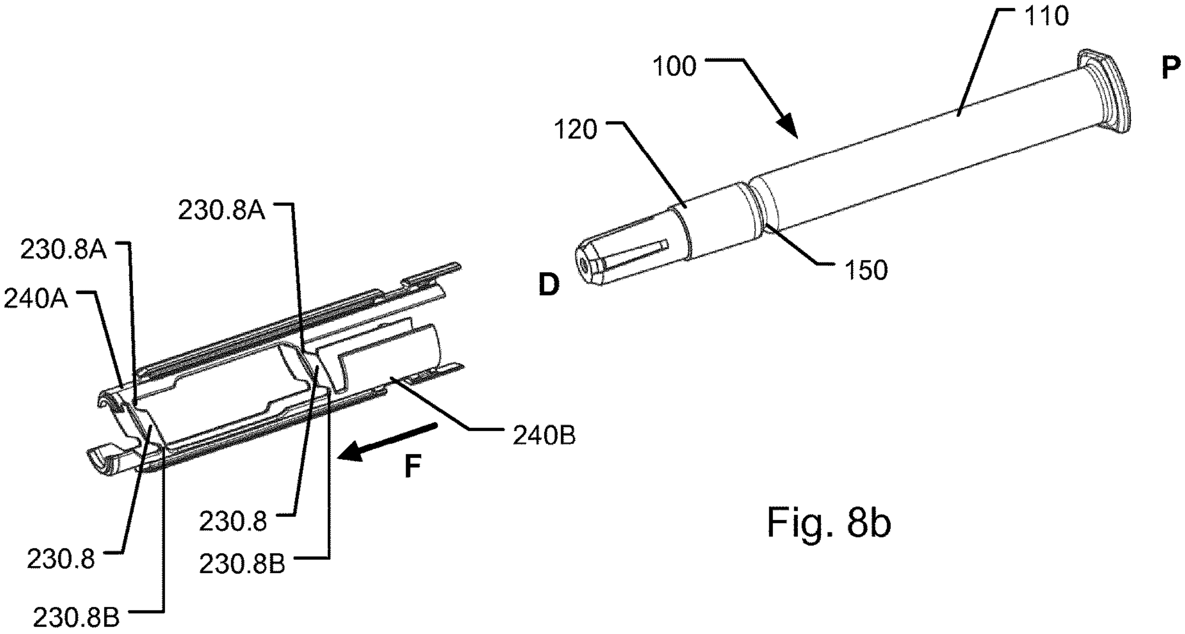

FIGS. 8*a* and 8*b* show two perspective side views of a syringe holder 200 according to a fourth embodiment in combination with a syringe 100 to be held by the syringe holder. The FIG. 8*a* view depicts the syringe holder 200 in a non-biased state wherein the syringe holder enables a syringe to be retained within the syringe holder. The FIG. 8*b* view shows the syringe holder in a biased or open state enabling insertion of a syringe into the syringe holder.

Figure 9A:
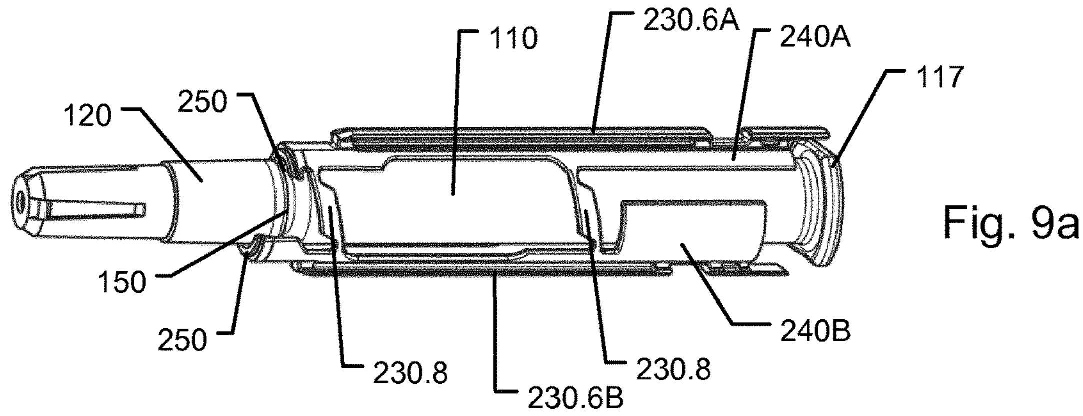
FIGS. 9*a* and 9*b* show perspective views of an assembly of a syringe 100 and a syringe holder 200 of the fourth embodiment, FIGS. 9*a* and 9*b* respectively showing the syringe holder in a biased state and in a non-biased state during assembly.
Figure 9B:
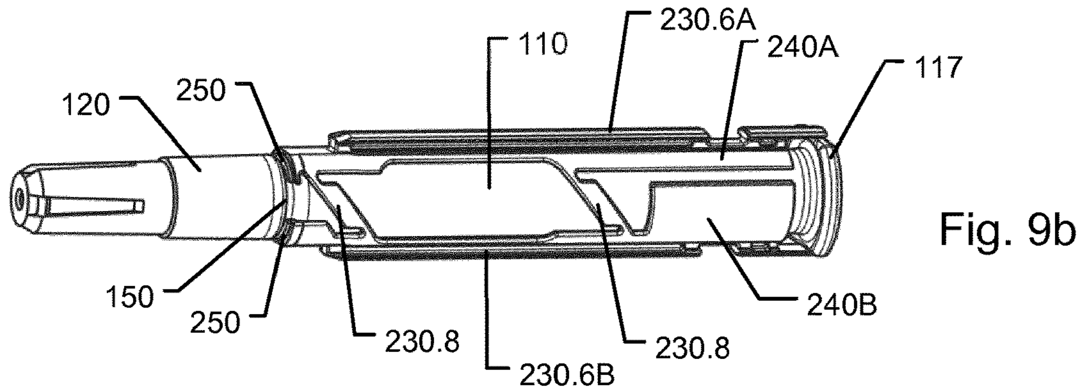

In FIG. 9*a* the syringe holder is shown in the open state, i.e. a non-retaining state, wherein a syringe 100 has been inserted axially through a proximal opening of the syringe holder 200. The syringe holder is still in the biased state where the syringe 100 is not axially retained relative to the syringe holder 200. FIG. 9*b* shows the syringe holder 200 in the non-biased state wherein two shoulder sections 250 of the body of the syringe holder axially align with the gap 150 formed between the barrel 110 and the needle shield 120, thus providing an axial retainment of the syringe in a manner generally corresponding to the previous described embodiments.

Figure 12A:
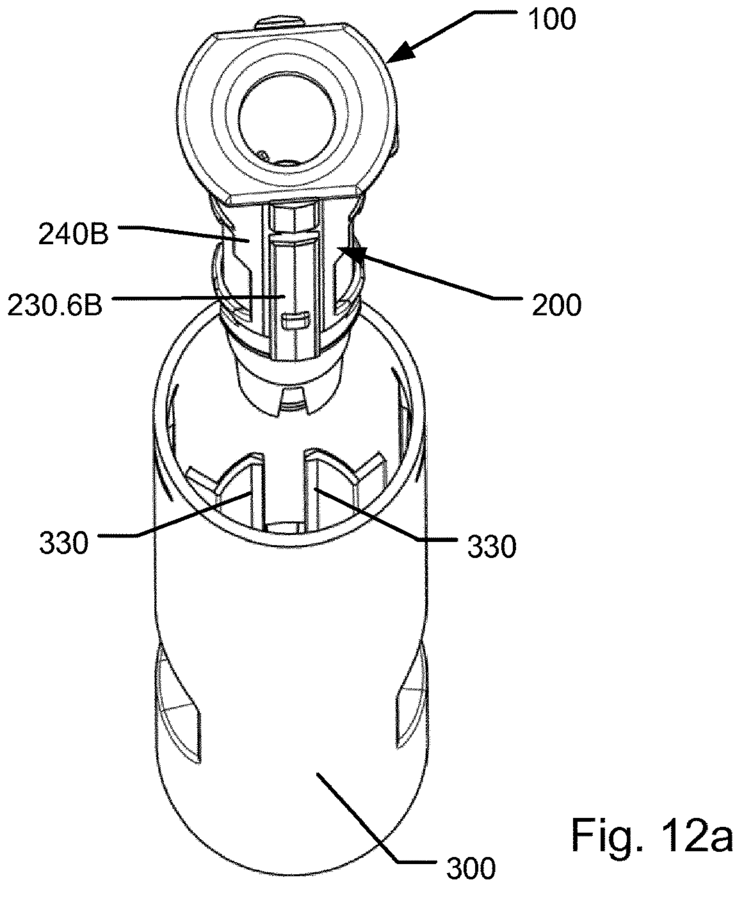
FIG. 12*a* shows a perspective rear view of a syringe holder assembly 100/200 of the fourth embodiment together with an outer housing 300 of an injection device in a state prior to insertion.

As indicated in FIG. 12*a*, the syringe holder 200 of the fourth embodiment is intended to form a dedicated syringe holder intended to define an internal component of an injection device. The syringe holder 200 in combination with a syringe 100 held fixedly by the syringe holder 200 may thus define a sub-assembly where the sub-assembly is intended for insertion into a separately formed outer housing 300, either in an axially fixed or in an axially slideable relationship relative to the outer housing 300.

Similar to the syringe holders according to the second and third embodiment described above, the syringe holder 200 of the fourth embodiment also includes a body 210 formed as a generally tubular outer shell extending along a central longitudinal axis and shaped to define a cylindrical open space suitable to receive the barrel 110 of a held syringe 100. The body 210 includes two longitudinally extending body sections 240A and 240B symmetrically arranged in an opposed manner around the central longitudinal axis. Each body section 240A/240B has a distal end with a shoulder section 250 adapted to engage a circumferential gap 150 between the barrel 110 of the syringe 100 and a needle shield 120, such as an RNS, covering the needle 130 of the syringe. In the state shown in FIG. 9*b* the shoulder sections 250 assume a retaining position wherein a proximally facing surface of each shoulder section 250 engages the neck portion 115 of the barrel 110 thus preventing the syringe 100 from moving in a distal direction (D) relative to the syringe holder 200. Each of the body sections 240A/240B define two longitudinal extending side edges generally running in parallel from the shoulder sections 250 arranged at the distal end to a proximal end of the body 210. In the shown embodiment, when a syringe 100 is held by the syringe holder 200, the proximal ends of body sections 240A/240B are located a distance from the finger flange 117 of the syringe 100. In this state, the two shoulder sections 250 both align axially with the circumferential gap 150.

Referring to FIGS. 8*a* and 8*b*, the two body sections 240A/240B are individually movable relative to each other so as to provide for movement in a radial direction by means of expandable connectors 230 arranged on either side of the body sections 240A/240B. Each of the expandable connectors 230 interconnects the two body sections 240A/240B at longitudinal extending edges thereof. Again, in this fourth embodiment, the two body sections 240A/240B, and thus the shoulder sections 250, are reversibly movable from the retaining position into the non-retaining position. In the shown fourth embodiment, the expandable connectors 230 are provided in form of a plurality of individual linkage sections 230.8 that are disposed longitudinally at respective axial locations along the body sections 240A, 240B. Opposing ends of each linkage section 230.8 connect to a respective body section 240A, 240B by means of a hinge 230.8A/230.8B formed as a living hinge. Each linkage section 230.8 is formed so that, when the body sections 240A, 240B assume their retaining position as shown in FIG. 9*b*, each linkage section 230.8 extends along an axis being tilted relative to the circumferential direction. In the shown embodiment, for each linkage section 230.8, an axis running through the opposing ends of each linkage section is inclined with respect to the circumferential direction, the inclination angle being around 40-45 deg. In other embodiments, the inclination angle may be designed assuming values outside this angle interval. As the shown embodiment provides a syringe holder having a generally cylindrical configuration, the linkage sections are arranged generally extending in a helical manner firmly around the barrel of held syringe.

Although the fourth embodiment shows the linkage sections to include dedicated hinges in form of reduced material portions at each ends of the linkage sections it is to be noted that the linkage sections, in accordance with the claimed invention and in accordance with the term "hinge", may include linkage sections which, even though no dedicated reduced material portions are provided, may act as hinges themselves by utilizing the resiliency of the material portion forming the linkage sections.

As shown in the embodiment of FIG. 8*a*, each longitudinal side edge of any of the body sections interconnect, via hinges, to the neighbouring side edge of the other of one of the other body sections by means of two individual linkage sections 230.8. In the shown embodiment, the first individual linkage section is arranged in the distal end of the body 210 whereas the second individual linkage section is arranged in the proximal half of the body 210. In the shown embodiment, the pairs of expandable connectors 230 between any two neighbouring edges of the body sections 240A, 240B are configured as a parallelogram configuration. Hence, the body sections are able to move radially relative to each other when one body section is moved in axial direction relative to the neighbouring body section.

Owing to the fact that the expandable connectors 230 i.e. linkage sections 230.8, are arranged at each longitudinal extending edge of the body 210 the syringe holder forms a closed loop in the circumferential direction. Due to the expandable connectors 230, the body 210 is circumferentially expandable and contractible so as to move the two body sections 240A/240B, and thus the shoulder sections 250, radially from the retaining position into the non-retaining position and back again into the retaining position. In the shown embodiment, the body 210 is circumferentially expandable and contractible. Hence, the two body sections 240A/240B are reversibly movable from the retaining position into the non-retaining position. In the fourth embodiment, the shoulder sections 250 assume the retaining position shown in FIGS. 8*a* and 9*b* when the syringe holder 200 assumes an unbiased state. However, in other embodiments, the shoulder sections 250 may assume the non-retaining position when the syringe holder 200 assumes an unbiased state. In still other embodiments, the shoulder sections 250 may assume an intermediate position between the retaining position and the non-retaining position when the syringe holder is in an unbiased state, or alternatively be configured to provide a radially inwards clamping force, when the shoulder sections assume the retaining position with a syringe accommodated within the body 210 of the syringe holder.

In the shown embodiment, the body 210 is provided by two opposing body sections that, wherein the neighbouring longitudinal edges of the respective body sections are interconnected by expandable connector arrangements 230 so that two expandable connector arrangements 230 are arranged in an opposed manner. In other embodiments, the number of body sections may be provided as three or more sections distributed around the circumference of a held syringe, where longitudinal edges of neighbouring body sections are interconnected by an expandable connector arrangement.

Figure 10A:
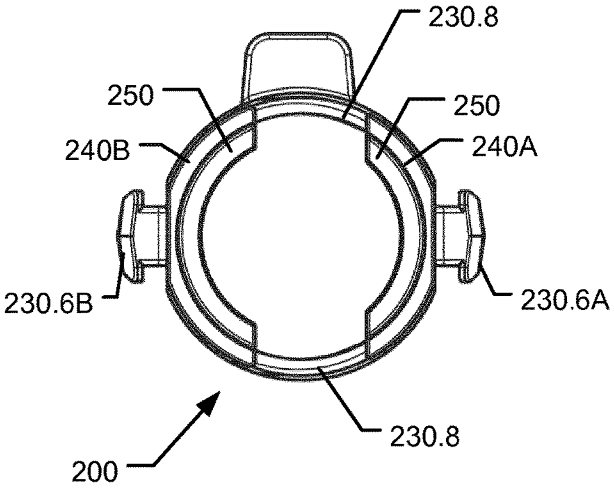
FIGS. 10*a*-10*b* show two distal end plane views of the syringe holder 200 of the fourth embodiment respectively showing the syringe holder in a non-biased state and a biased state.
Figure 10B:
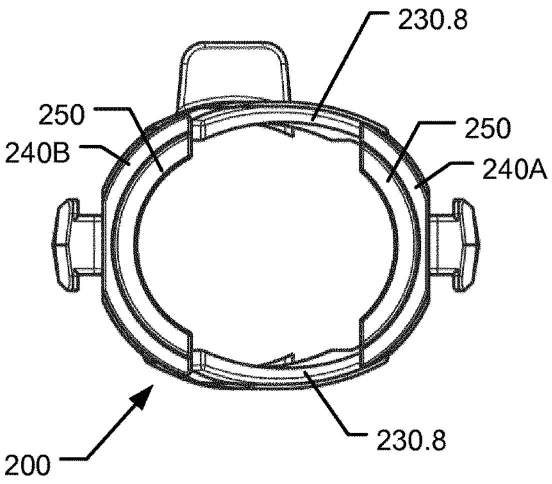
Figure 10C:
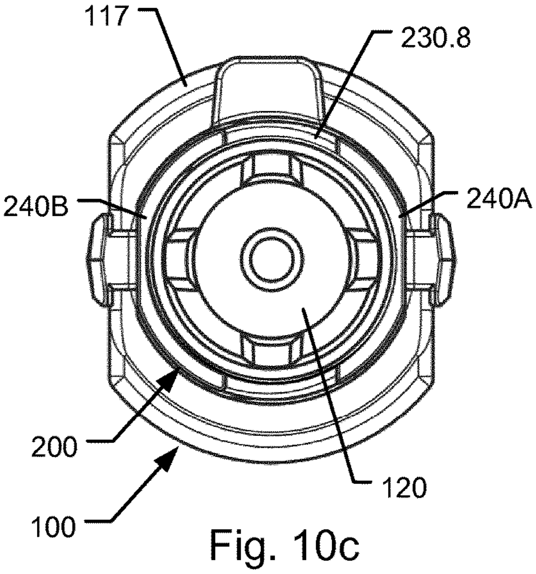
FIGS. 10*c*-10*d* are views that correspond with the views of FIGS. 10*a*-10*b*, but additionally showing a syringe which has been inserted into the syringe holder.
Figure 10D:
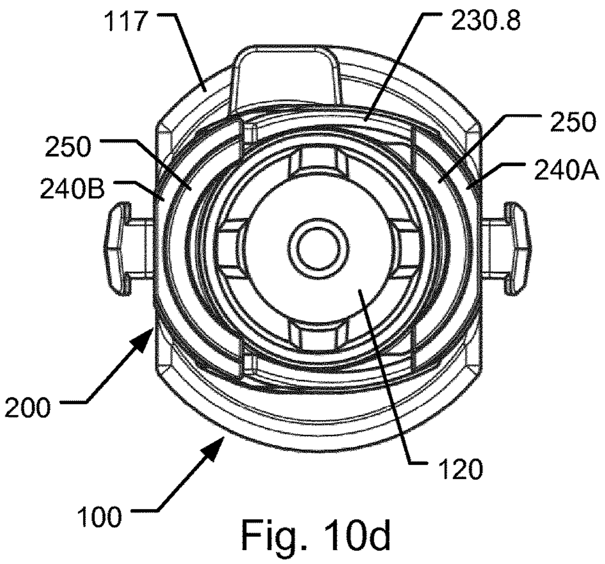

The syringe holder 200 according to the fourth embodiment is further shown in FIGS. 10*a*-10*b* which are two distal end plane views of the syringe holder respectively showing the syringe holder in the non-biased state and the biased state, whereas FIGS. 10*c*-10*d* show corresponding views additionally showing a syringe 100 with needle shield 120 which has been inserted into the syringe holder.

Referring to FIG. 10*a* and also to FIGS. 9*a* and 9*b*, the body section 240A includes a longitudinally running rib 230.6A which protrudes radially outwards from body section 240A along a substantial part of its length. A corresponding rib 230.6B is formed to protrude radially outwards from body section 240B. From FIG. 10*a*, when viewed in cross section orthogonally to the longitudinal axis, it is apparent that the ribs 230.6A and 230.6B each are formed to have a narrow connecting portion that radially inwardly connects to the body section and radially outwardly connects to a free enlarged head section.

FIGS. 11*a*-11*f* show a series of perspective side views of the syringe holder 200 according to the fourth embodiment together with a tool arrangement 500A/500B, the series of views schematically providing a representation of various stages during assembly operations. The tool arrangement is configured to manipulate syringe holder 200 in a manner to move the body section 240B axially relative to body section 240A so as to cause the two body sections to move radially outwards relative to each other enabling a syringe to be inserted into the syringe holder.

Figure 11A:
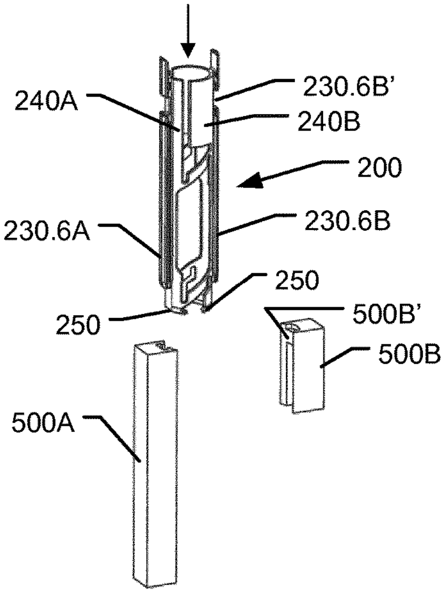
FIGS. 11*a*-11*f* are schematic views of the syringe holder 200 of FIG. 8*a* together with a tool arrangement 500 and a syringe 100, the individual views representing different states during assembly operations.

Referring to FIG. 11*a*, the tool arrangement comprises first and second tool parts, i.e. a first body section fixture 500A and a second body section fixture 500B. The first body section fixture 500A includes a longitudinal track witch is axially open at the proximal end of the tool holder 500A. The axial open track is configured to receive the longitudinal rib 230.6A of body section 240A of an inserted syringe holder. As a first step, the syringe holder 200 is moved axially in the distal direction into the axially open track of body section holder.

Figure 11B:
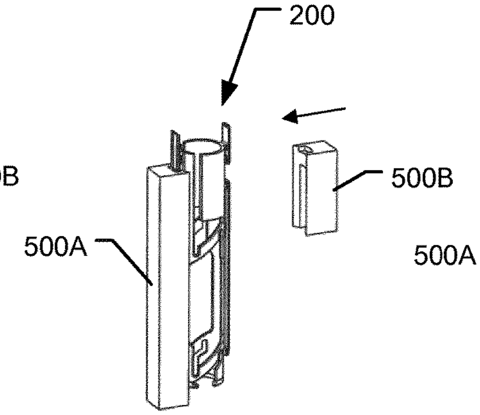
Figure 11C:
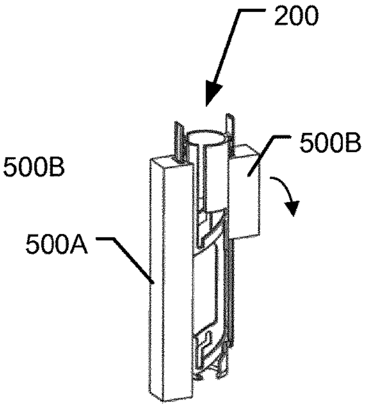

As seen in FIG. 11*b*, the syringe holder 200 has been inserted into the first body section fixture 500A and is fixedly held therein both with respect to axial and to radial movement. A second body section fixture 500B includes an axially extending recess configured to receive the longitudinal rib 230.6B of body section 240B of an inserted syringe holder. The axially extending recess ends with a protrusion 500B' which is configured to be received within a recess 230.6B' formed in the longitudinal rib 230.6B of a syringe holder. The second body section fixture 500B is moved radially towards the held syringe holder 200 so that the protrusion 500B' is received within recess 230.6B'. This state is shown in FIG. 11*c*. The second body section fixture 500B is then moved axially in the distal direction relative to first body section fixture 500A in a combined axial and radial movement in agreement with the movement defined by the linkage sections 230.8 of the syringe holder 200. Hence, the body sections 240A and 240B are moved radially away from each other.

Figure 11D:
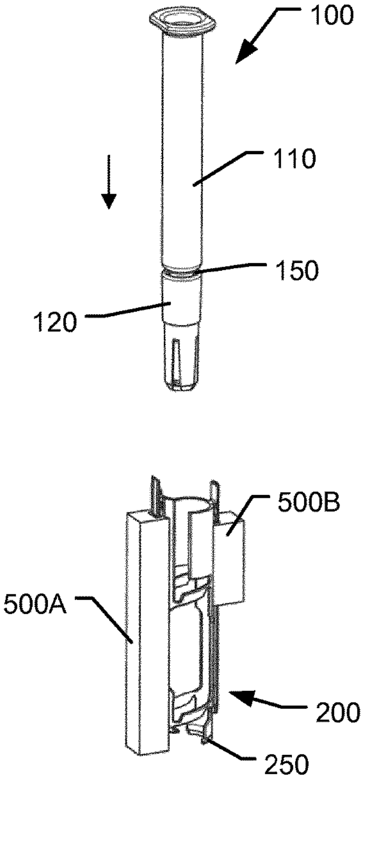
Figure 11E:
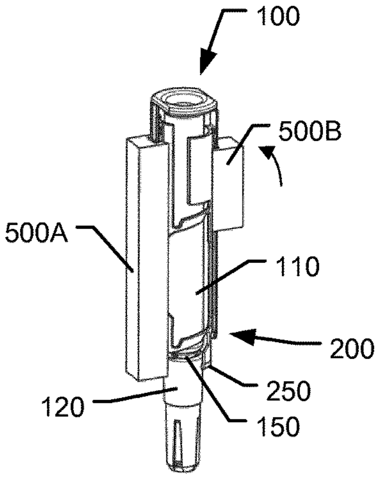
Figure 11F:
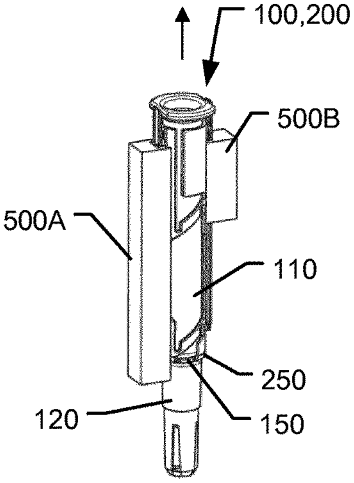

In FIG. 11*d* a syringe 100 is inserted distally into the open syringe holder 200 until the gap 150 aligns axially with shoulder section 250 of body section 240A. This is shown in the stage depicted in FIG. 11*e* wherein the second body section fixture 500B is then moved axially in the proximal direction relative to first body section fixture 500A in a combined axial and radial movement, again in agreement with the movement dictated by the linkage sections 230.8 of syringe holder 200. Hence, the body sections 240A and 240B are moved radially towards each other until both shoulder section 250 are axially aligned with gap 150 and engagement between the barrel of the held syringe is engaged by both shoulder sections 250. As shown in FIG. 11*f*, after the second body section fixture 500B is moved radially away from the held syringe holder 200, the assembly of syringe holder 200 and syringe 100 may be removed from the first body section fixture 500A by moving the assembly 100/200 in the proximal direction. In the assembly 100/200, the syringe 100 is prevented from moving distally relative to the syringe holder 200 and the assembly can be thereafter be handled safely as one unit.

The assembly 100/200 may be used in combination with other components forming part of a medical injector assembly. As shown in FIG. 12*a*, and further in FIGS. 12*b*-12*d*, the syringe and syringe holder assembly 100/200 may be inserted into a separately formed outer housing 300. The assembly formed by the outer housing, the syringe holder and the syringe, will optionally be combined with additional components, to form a medical injector, such as an autoinjector. The shown outer housing 300 comprises a plurality of interface geometries that protrude radially inwards from an outer shell portion 310 of the housing 330, the interface geometries being configured for engaging and receiving the longitudinal ribs 230.6A and 230.6B of the syringe holder 200.

Figure 12B:
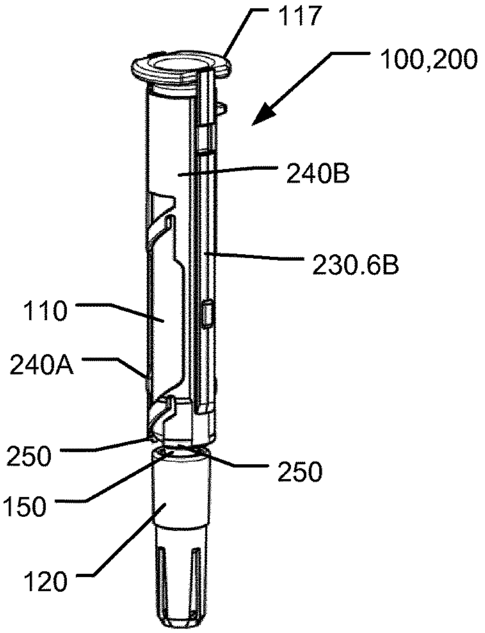
FIGS. 12*b*-12*d* show a series of perspective views of the components shown in FIG. 12*a*, the series of views representing different states during insertion of the syringe and syringe holder assembly 100/200 into the outer housing 300.
Figure 12B:
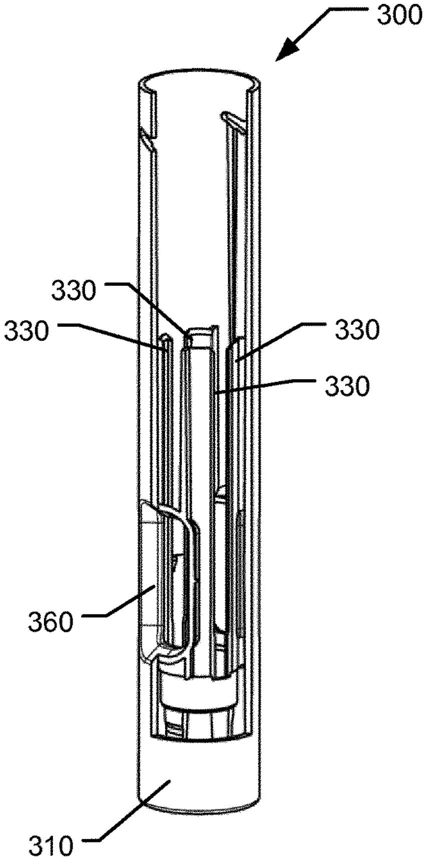
Figure 12C:
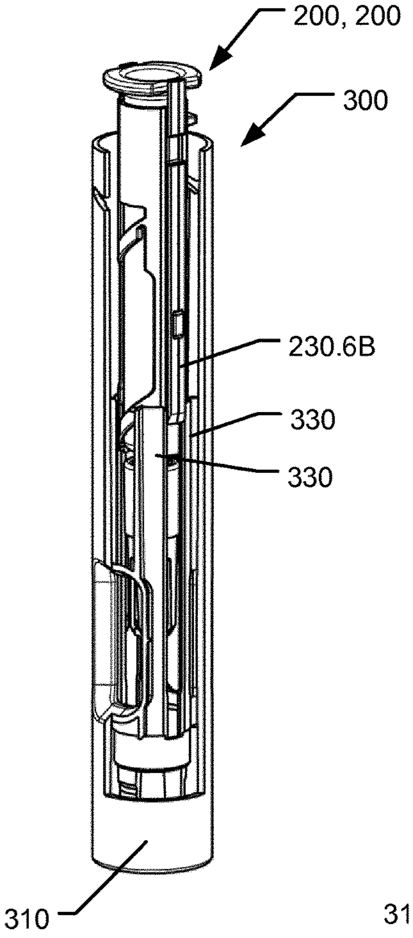
Figure 12D:
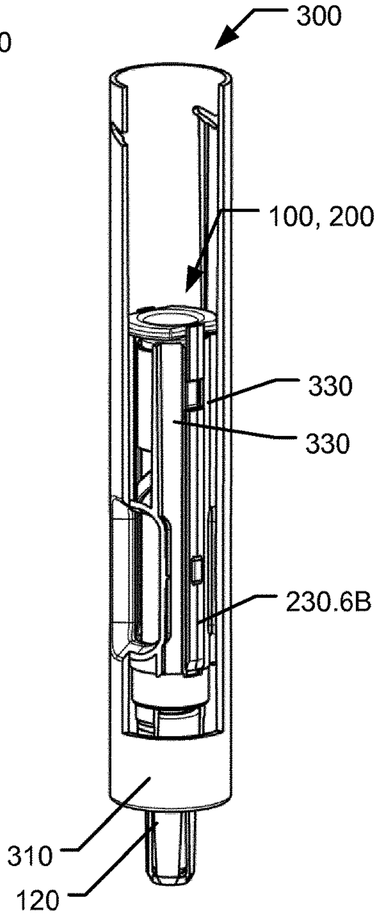

As shown in FIG. 12*b*, the interface geometries of the outer housing 300 include four separate guides 330 each of which are formed to extend in the longitudinal direction in parallel with the central longitudinal axis. In the shown embodiment, the four guides 330 are arranged pairwise to define longitudinal extending rails arranged with a narrow axial running gap between the rails (see also FIG. 12*a*). Each pair of guides 330 is configured to engage a respective one of the longitudinal ribs 230.6A and 230.6B of an inserted syringe holder 200 so that the narrow connecting portion and the free enlarged head section of the respective rib is received within the gap between rails and thus radially fixed by cooperating with the rails. The syringe and syringe holder assembly 100/200 is inserted in the distal direction through a proximal opening of the outer housing 300 as shown in FIGS. 12*c* and 12*d*. In the assembled state, by cooperating with the guides 330, the two body sections 240A/240B of the syringe holder 200 are retained with the shoulder sections 250 in the retaining position. Further interface geometries are provided for controlling the axial position of the syringe and syringe holder assembly 100/200 inside the outer housing, such as by engaging distally facing surface areas of the body sections 240A and 240B at the vicinity of shoulder sections 250. Hence, the two body sections 240A/240B are prevented from being moved away from each other and are fixedly positioned with the shoulder sections 250 in the retaining position. This state is maintained even when forces are applied onto the syringe in the distal direction, such as typically occurring during use of the medical injector, e.g. during administration wherein a distally directed force is exerted on the slideable piston 140 inside the syringe 100, or upon an impact which may be caused by accidentally dropping the device onto a hard surface.

As shown in the drawings the outer housing 300 may be formed to define window openings 360 which align with the window openings 260 of the syringe holder 200 when the syringe and syringe holder assembly 100/200 has been properly inserted into outer housing 300. This will enable the user to visually inspect the drug contained in the syringe.

Figure 13A:
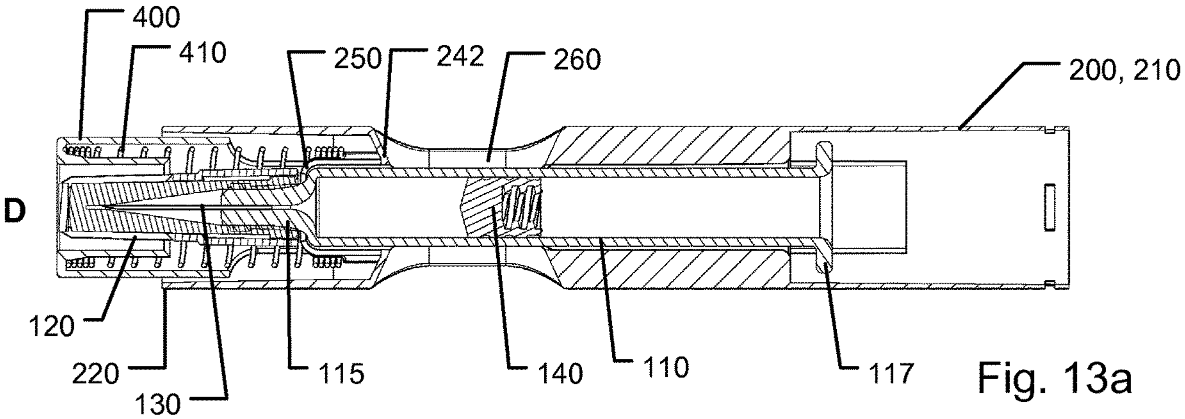
FIG. 13*a* shows a cross sectional side view of key components of an injection device with a syringe holder 200 in accordance with a fifth embodiment.

FIG. 13*a* schematically shows a cross sectional view of key components of an injection device with a syringe holder 200 of a fifth embodiment. The syringe holder 200 again accommodates a syringe 100 of the type shown in FIG. 1. In the fifth embodiment, the syringe holder is formed integrally with a housing and thus directly retains the syringe within the housing of the injection device. Typically, the injection device will include additional components, such as components relating to an expelling assembly, but for clarity these components have been omitted from view.

The syringe holder 200 includes a body 210 generally formed as tubular outer shell with a distal rim portion 220 arranged pointing in the distal direction adjacent the needle 130 of the held syringe 100. The tubular outer wall of body 210 includes a proximal opening arranged to receive syringe 100. In order to retain the syringe 100 inside syringe holder 200, the outer wall of body 210 comprises, on a radially facing inner surface, a series of support structures 242 each having a shoulder section 250 pointing radially inwards at an axial location near the distal rim portion 220 of the tubular outer wall of body 210. Each of the support structures 242 provides a body section for the syringe holder, in the embodiment formed as four individual support structures that are arranged in a circular configuration at the same axial position inside the tubular outer wall. Each of the shoulder sections 250 define an arcuate surface portion shaped for being received into the gap 150 between the barrel 110 and the needle shield 120 of a held syringe 100, i.e. so that the shoulder sections engages the neck portion 115 of barrel 110 when the syringe is properly retained within the syringe holder. In the shown fifth embodiment, the syringe holder 200 includes four individual shoulder sections 250. However, other embodiments may include a smaller or higher number of individual support structures 242 or shoulder sections 250, such as two, three or more than four.

As with the other embodiments described above, the shoulder sections 250 serve to retain the syringe 100 when situated within the syringe holder 200. The shoulder sections 250 are movable due to inherent resilience of the four individual support structures 242 between a retaining position (shown in FIG. 13*a*) where the shoulder sections 250 assume a radially inwards position and a non-retaining position (not shown) where the shoulder sections assume a radially outwards position. In the radially outwards position, the syringe, with the needle shield 120 attached, is insertable axially so that the circumferential gap 150 is positioned and axially aligns with the shoulder sections 250. In the radially inwards position the shoulder sections 250 engage the neck portion 115 of the barrel of the syringe and provide a seat for the syringe.

In the fifth embodiment, further to the syringe holder 200 and syringe 100, the shown key components of the injection device also include a needle shroud 400 and a needle shroud spring 410. In the shown embodiment, the needle shroud 400 is formed as a tubular sleeve which encircles the needle end of the syringe 100. The needle shroud further comprises a distal end surface configured to be held against an injection site. The central portion of the distal end face includes a needle aperture through which the needle 130 of the syringe 100 is configured to protrude.

The needle shroud 400 is movable translationally along a central axis of the housing and thus axially movable relative to the syringe holder 200 and the held syringe 100. In FIG. 13*a*, the needle shroud 400 assumes a distal extended position wherein the needle shroud covers the needle. Upon a proximal direction force exerted upon the distal end face of the needle shroud 400 the needle shroud is movable into a not shown proximal collapsed position wherein the injection needle 130 protrudes through the needle aperture.

The needle shroud 400, at the distal end thereof, further includes a proximal facing annular surface serving as a first spring seat for the needle shroud spring 410. Each of the support structures 242 includes axially extending ribs 243 arranged on the radial outer surface of the support structure, The axially extending ribs 243 provides in combination a second spring seat for the needle shroud spring 410. The needle shroud spring 410 is provided as a helical compression spring having closed windings of material at both ends while having open windings in between. The needle shroud spring 410 is arranged axially compressed between the first spring seat and the second spring seat. The needle shroud spring thus provides a biasing force onto the first spring seat so that the needle shroud 400 is urged towards the distal extended position.

Figure 13B:
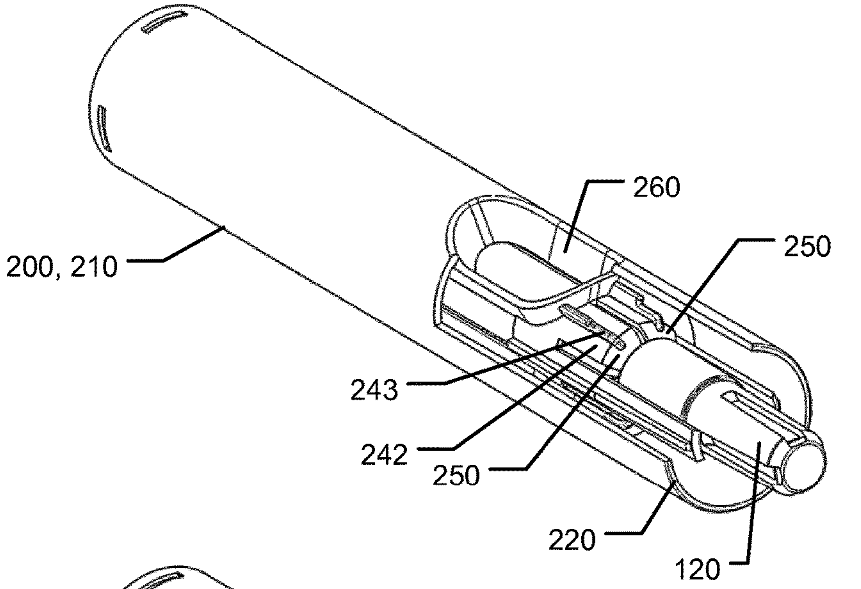
FIGS. 13*b* and 13*c* show partly cut perspective views of an assembly of the injection device of FIG. 13*a* in different assembly conditions.
Figure 13C:
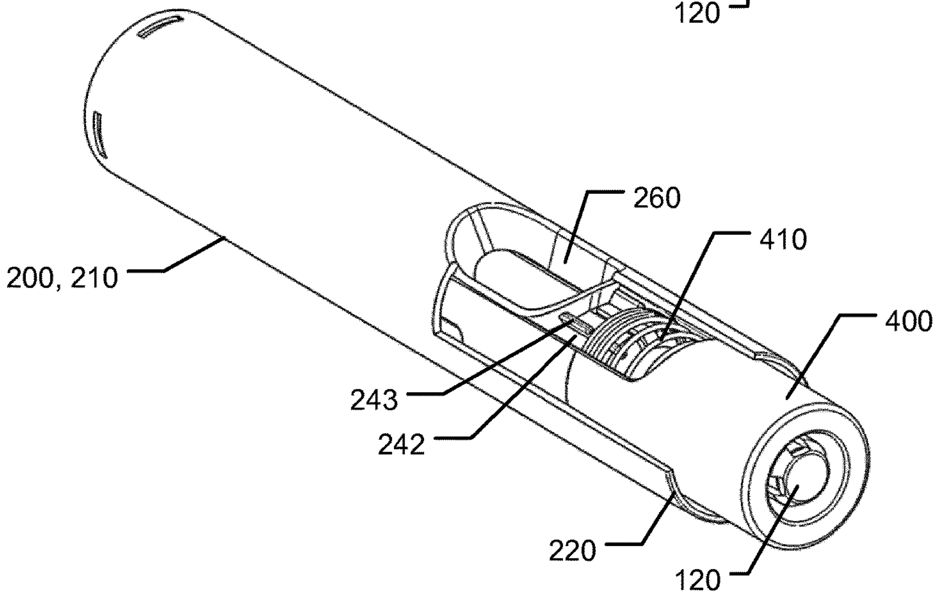

FIGS. 13*b* and 13*c* show a series of perspective partly cut views of the syringe holder 200 together with a syringe 100 wherein the two views are representative for two different states during assembly of the injection device.

In the state shown in FIG. 13*b* the needle shroud spring 410 and the needle shroud 400 have not yet been assembled with the syringe holder 200. However, the syringe 100 with the needle shield 120 attached have been moved into the syringe holder into a position wherein the shoulder sections 250 assume their radially inwards position where they engage the neck portion 115 of the barrel of the syringe. In this state the shoulder sections 250 would be movable radially outwards, due to the resiliency of the support structures 242, if the syringe where to be forced distally relative to the syringe holder.

In the state shown in FIG. 13*c* the needle shroud spring 410 is properly seated relative to the syringe holder 200 so that a proximal portion of the needle shroud spring 410 encircles the support structures 242 with a plurality of the closed windings of the needle shroud spring encircling the axially extending ribs 243. Further, in FIG. 13*c*, the needle shroud 400 has been inserted into sliding engagement with the body 210 of the syringe holder 200 wherein a not shown retaining mechanism has been established for preventing the needle shroud 400 to move further distally relative to the distal extended position. The plurality of windings of the needle shroud spring 410 that engages the axially extending ribs 243 of the support structures 242 provide a radially inwards compression force onto the support structures, serving to arrest the support structures in a position where the shoulder sections 250 assume their radially inwards position. Referring to the assembly state shown in FIG. 13*c*, as the shoulder sections 250 themselves are sufficiently rigid to firmly retain the syringe 100 without the shoulder sections being able to flex when large distal directed forces are exerted onto the syringe 100, the syringe 100 is prevented from moving distally relative to the syringe holder. This enables, initially, the needle shield 120 to be removed from the syringe 100, and the subsequent expelling procedure of drug from the syringe 100 to be carried out, both of these procedures resulting in substantial distal forces being exerted onto the held syringe.

In the design shown, the syringe holder 200 according to the fifth embodiment is intended to form an outer housing of a medical injector. In the shown embodiment, the syringe is thus held directly by the outer housing. Hence, the design dispenses with the requirement of having further dedicated components for holding the syringe within the outer housing, e.g. preventing the syringe from uncontrolled movements in the distal direction relative to the outer housing.

In other not shown embodiments, a syringe holder provided in accordance with the general principle shown in FIGS. 13*a* through 13*c*, may be designed to form a dedicated syringe holder intended to define an internal individual component of an injection device. The syringe holder, in combination with a syringe being held by the syringe holder, may thus define a sub-assembly which is intended to be inserted into a separately formed outer housing, either in an axially fixed or in an axially slideable relationship.

As will be readily recognized by the skilled reader, the medical injectors described above may also include various other components to provide different functions. The description above with respect to the figures has been provided to give background information on the use of exemplary syringe holders suitable for use with various types of injection devices. However, the exemplary injection devices touched upon in the present disclosure is a subset of many different available injection devices that can be utilized with the principles according to the present invention.

It should be stressed that the invention is not limited to the shown embodiments and the described variants, but may be embodied in other ways within the subject matter defined in the following claims and within the remaining disclosure.

The invention claimed is:

1. A syringe holder for insertion into an outer housing of a medical injector, comprising:

a body extending along a central longitudinal axis and adapted to receive the barrel of a syringe, wherein the body includes at least two body sections disposed around the central longitudinal axis, the body sections having distal ends with shoulder sections adapted for being received in a circumferential gap between the barrel of the syringe and a needle shield covering a needle of the syringe to retain the syringe so as to prevent the syringe from moving distally (D) relative to the syringe holder, wherein the syringe holder is made from a resiliently deformable material and wherein the body further comprises a plurality of connector arrangements each interconnecting pairs of the at least two body sections, wherein each connector arrangement comprises a portion forming at least one linkage section forming an expansion connector arrangement(s) so that the body sections and the expansion connector arrangements form a continuous closed loop in a circumferential direction around the barrel of a syringe held by the body and so that the body sections are movable radially relative to each other between a non-retaining position and a retaining position while maintaining the continuous closed loop, and wherein each expansion connector arrangement is either:

formed to comprise two or more linkage sections arranged in a concertina configuration in the circumferential direction of the body, or provided as at least one linkage section, wherein opposing ends of the linkage section connect to a respective body section by way of a hinge, wherein the linkage section comprises a linkage section segment being inclined with an angle of inclination relative to the circumferential direction when the body sections assume their retaining position, and wherein the body sections are movable axially relative to each other so that the body sections are forced to move radially as the body sections move axially relative to each other.

2. The syringe holder as defined in claim 1, wherein the plurality of expansion connector arrangements are formed to enable circumferential contraction of the body sections from the non-retaining position to the retaining position.

3. The syringe holder as defined in claim 2, wherein the plurality of expansion connector arrangements are formed to enable circumferential expansion of the body sections from the retaining position to the non-retaining position.

4. The syringe holder as defined in claim 1, wherein each body section extends from said distal end to a proximal end, and wherein both the distal end and the proximal end of each body section are movable in radial direction relative to the other of the at least two body sections.

5. The syringe holder as defined in claim 1, wherein the expansion connector arrangements are formed to enable the body sections to be movable radially so that the body sections are individually movable to assume a substantially parallel configuration in the non-retaining position and to assume a substantially parallel configuration in the retaining position.

6. The syringe holder as defined in claim 1, wherein said linkage section comprises said linkage section segment being inclined with an angle of inclination relative to the circumferential direction when the body sections assume their retaining position, and wherein each expansion connector arrangement between longitudinal edge portions of any two neighbouring body sections are provided as a plurality of individual linkage sections disposed longitudinally at respective axial locations along the body sections.

7. The syringe holder as defined in claim 6, wherein said angle of inclination between the linkage section segment and the circumferential direction is increased as the body sections are moved from the non-retaining position to the retaining position as the body sections undergoes relative axial movement.

8. The syringe holder as defined in claim 7, wherein said plurality of individual linkage sections between any two neighbouring body sections are configured as a parallelogram configuration.

9. A medical injector comprising a syringe holder as defined in claim 1, and further comprising a syringe having a barrel and a needle shield covering a needle of the syringe, wherein a circumferential gap is provided between the barrel of the syringe and the needle shield, wherein the barrel of the syringe is received in the body, and wherein the shoulder sections are positioned within the circumferential gap.

10. The medical injector as defined in claim 9, wherein the medical injector further comprises an outer housing, and wherein the outer housing comprises one or more interface geometries engaging interface geometries of the syringe holder for positioning the syringe holder relative to the outer housing, and wherein the interface geometries of the housing exert a clamping force onto the syringe holder acting to retain the body sections in the retaining position.

11. The medical injector as defined in claim 10, wherein the syringe holder further comprises an expansion connector arrangement between longitudinal edge portions of any two neighbouring body sections are provided as at least one linkage section, wherein opposing ends of the linkage section connect to a respective body section by way of a hinge, wherein the linkage section comprises a linkage section segment being inclined with an angle of inclination relative to the circumferential direction when the body sections assume their retaining position, and wherein the body sections are movable axially relative to each other so that the body sections are forced to move radially as the body sections move axially relative to each other, and wherein the one or more interface geometries of the outer housing comprise a clamping structure configured to engage cooperating clamping surfaces of the expansion connector arrangements to clamp the two or more linkage sections of the concertina configuration towards each other so that the body sections are retained in the retaining position.

12. A method of forming a medical injector assembly comprising a syringe holder as defined in claim 1 and a syringe, wherein the method comprises the steps of:

a) providing the syringe comprising a barrel, a needle attached to the distal end of the barrel and a needle shield covering the needle of the syringe, wherein a circumferential gap is provided between the barrel and the needle shield, b) providing the syringe holder with the body sections assuming the non-retaining position, c) placing the syringe in the syringe holder, d) moving the body sections from the non-retaining position to the retaining position such that the shoulder sections are received within the circumferential gap between the barrel of the syringe and a needle shield covering a needle of the syringe to prevent the syringe from moving distally (D) relative to the syringe holder.

13. The method of forming a medical injector assembly as defined in claim 12, wherein the method step b) further comprises the step of positioning the syringe holder relative to a tool comprising at least first and second tool parts, and wherein the method step d) further comprises the steps of engaging respective ones of the at least first and second tool parts with respective ones of the at least at least two body sections, and positioning the at least first and second tool parts relative to each other thereby moving the body sections from the non-retaining position to the retaining position.

14. The method of forming a medical injector assembly as defined in claim 12, wherein the method step b) further comprises the steps of positioning the syringe holder relative to a tool comprising at least first and second tool parts, engaging respective ones of the at least first and second tool parts with respective ones of the at least at least two body sections and positioning the at least first and second tool parts relative to each other thereby moving the body sections to the non-retaining position.

15. The method of forming a medical injector assembly as defined in claim 12, wherein the method, subsequent to step d), further comprises the steps of:

e) providing an outer housing, wherein the outer housing comprises one or more interface geometries, f) inserting the syringe holder with the syringe held by the syringe holder relative to the outer housing so that the interface geometries of the housing engage the body of the syringe holder for maintaining the body sections in the retaining position.

* * * * *